United States Patent
Carini

(10) Patent No.: US 6,849,631 B2
(45) Date of Patent: Feb. 1, 2005

(54) SEMICARBAZIDES AND THEIR USES

(75) Inventor: David J. Carini, Wilmington, DE (US)

(73) Assignee: Bristol Myers Squibb Pharma Company, Princeton, NJ (US)

( * ) Notice: Subject to any disclaimer, the term of this patent is extended or adjusted under 35 U.S.C. 154(b) by 160 days.

(21) Appl. No.: 10/010,979

(22) Filed: Dec. 7, 2001

(65) Prior Publication Data

US 2002/0091127 A1 Jul. 11, 2002

Related U.S. Application Data

(60) Provisional application No. 60/254,116, filed on Dec. 8, 2000.

(51) Int. Cl.$^7$ .................. C07D 401/12; C07D 403/12; C07D 417/12; C07D 407/12; C07D 407/14
(52) U.S. Cl. .................. 514/253.01; 514/254.08; 514/218; 514/316; 514/322; 514/365; 540/575; 544/359; 544/360; 544/364; 544/371; 546/186; 546/199; 548/181
(58) Field of Search ................ 544/359, 360, 544/364, 371; 540/575; 546/186, 199; 548/181; 514/253.01, 254.08, 218, 316, 322, 365

(56) References Cited

U.S. PATENT DOCUMENTS

| | | | |
|---|---|---|---|
| 6,107,305 A | 8/2000 | Misra et al. | 514/303 |
| 6,114,365 A | 9/2000 | Pevarello et al. | 514/371 |

FOREIGN PATENT DOCUMENTS

| | | |
|---|---|---|
| GB | 2223946 A | 4/1990 |
| WO | WO99/17769 | 4/1999 |
| WO | WO99/54308 | 10/1999 |
| WO | WO00/27822 | 5/2000 |

OTHER PUBLICATIONS

Mani et al., Exp. Opin. Invest. Drugs, 2000, 9 (8), 1849–1870.
Jiang et al., Proc. Natl. Acad. Sci. USA, 1993, 90, 9026–9030.
Quaraishi, IL Farmaco, 1989, 44, 753–757.
Hosoi et al., J. Biochem., 1995, 117, 741–749.
Kamb et al., Science, 1994, 264, 436–440.
Bible et al., Cancer Research, 1997, 57, 3375–3380.
Russo et al., Nature, 1996, 382, 325–331.
Sherr, Cell, 1993, 73, 1059–1065.
Wang et al., Nature, 1990, 343, 555–557.
Chem Abstracts: JP60–130521/PN.
Chem Abstracts: JP62–099361/PN.
Pardee, Science, 1989, 246, 603–608.

*Primary Examiner*—Bruck Kifle
(74) *Attorney, Agent, or Firm*—Elliott Korsen; Rena Patel

(57) ABSTRACT

The present invention relates to the synthesis of a new class of indeno [1,2-c]pyrazol-4-ones of formula (I):

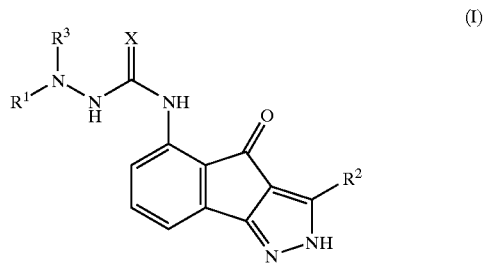

that are potent inhibitors of the class of enzymes known as cyclin dependent kinases, which relate to the catalytic subunits cdk1-7 and their regulatory subunits know as cyclins A-G.

This invention also provides a novel method of treating cancer or other proliferative diseases by administering a therapeutically effective amount of one of these compounds or a pharmaceutically acceptable salt form thereof. Alternatively, one can treat cancer or other proliferative diseases by administering a therapeutically effective combination of one of the compounds of the present invention and one or more other known anti-cancer or anti-proliferative agents.

38 Claims, No Drawings

SEMICARBAZIDES AND THEIR USES

CROSS-REFERENCE-TO-RELATED APPLICATION

This Application claims priority from provisional U.S. Application Ser. No. 60/254,116, filed Dec. 8, 2000, incorporated herein by reference in its entirety.

FIELD OF THE INVENTION

This invention relates generally to novel 5-substituted-indeno [1,2-c]pyrazol-4-ones which are useful as cyclin dependent kinase (cdk) inhibitors, pharmaceutical compositions comprising the same, methods for using the same for treating proliferative diseases, and intermediates and processes for making the same.

BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a diverse set of cellular signals both within the cell and from external sources. A complex network of tumor promoting and suppressing gene products are key components of this cellular signaling process. Over expression of the tumor promoting components or the subsequent loss of the tumor suppressing products will lead to unregulated cellular proliferation and the generation of tumors (Pardee, *Science* 246:603–608, 1989).

Cyclin dependent kinases (cdks) play a key role in regulating the cell cycle machinery. These complexes consist of two components: a catalytic subunit (the kinase) and a regulatory subunit (the cyclin). To date, nine kinase subunits (cdk 1–9) have been identified along with several regulatory subunits (cyclins A–H).(A. M. Senderowicz and E. A. Sausville Journal of the National Cancer Institute (2000), 92 (5), 376–387; and S. Mani; C. Wang; K. Wu; R. Francis; R. Pestell Exp. Opin. Invest. Drugs (2000) 9(8), 1849–1870).

Each kinase associates with a specific regulatory partner and together make up the active catalytic moiety. Each transition of the cell cycle is regulated by a particular cdk complex: G1/S by cdk2/cyclin E, cdk4/cyclin D1 and cdk6/cyclinD2; S/G2 by cdk2/cyclin A and cdk1/cyclin A; G2/M by cdk1/B. The coordinated activity of these kinases guides the individual cells through the replication process and ensures the vitality of each subsequent generation (Sherr, *Cell* 73:1059–1065, 1993; Draetta, *Trends Biochem. Sci.* 15:378–382, 1990).

An increasing body of evidence has shown a link between tumor development and cdk related malfunctions. Over expression of the cyclin regulatory proteins and subsequent kinase hyperactivity have been linked to several types of cancers (Jiang, *Proc. Natl. Acad. Sci. USA* 90:9026–9030, 1993; Wang, *Nature* 343:555–557, 1990). More recently, endogenous, highly specific protein inhibitors of cdks were found to have a major affect on cellular proliferation (Kamb et al, *Science* 264:436–440, 1994; Beach, *Nature* 336:701–704, 1993). These inhibitors include p16$^{INK4}$ (an inhibitor of cdk4/D1), p21$^{CIP1}$ (a general cdk inhibitor), and p27$^{KIP1}$ (a specific cdk2/E inhibitor). A recent crystal structure of p27 bound to cdk2/A revealed how these proteins effectively inhibit the kinase activity through multiple interactions with the cdk complex (Pavletich, *Nature* 382:325–331, 1996). These proteins help to regulate the cell cycle through specific interactions with their corresponding cdk complexes. Cells deficient in these inhibitors are prone to unregulated growth and tumor formation.

Protein kinases, in particular, CDK, play a role in the regulation of cellular proliferation. Therefore, CDK inhibitors could be useful in th treatment of cell proliferative disorders such as cancer, familial adenomatosis polyposis, neuro-fibromatosis, psoriasis, fungal infections, endotoxic shock, trasplantaion rejection, vascular smooth cell proliferation associated with atherosclerosis, pulmonary fibrosis, arthritis glomerulonephritis and post-surgical stenosis and restenosis (U.S. Pat. No. 6,114,365. CDKs are also known to play a role in apoptosis. Therefore CDK inhibitors, could be useful in the treatment of useful of cancer; viral infections, for example, herpevirus, poxvirus, Epstein-Barr virus, Sindbis virus and adenovirus; prevention of AIDS development in HIV-infected individuals; autoimmune diseases, for example, systemic lupus, erythematosus, autoimmune mediated glomerulonephritis, rheumatoid arthritis, psoriasis, inflammatory bowel disease, and autoimmune diabetes mellitus; neurodegenerative disorders, for example, Alzheimer's disease, AIDS-related dementia, Parkinson's disease, amyotrophic lateral sclerosis, retinitis pigmentosa, spinal muscular atrophy and cerebellar degeneration; myelodysplastic syndromes, aplastic anemia, ischemic injury associated with myocardial infarctions, stroke and reperfusion injury, arrhythmia, atherosclerosis, toxin-induced or alcohol related liver diseases, hematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain (U.S. Pat. No. 6,107,305).

It has also been discovered that some cyclin-dependent kinase inhibitors can be used in combination therapy with some other anticancer agents. For example, the cytotoxic activity of the cyclin-dependent kinase inhibitor, flavopiridol, has been used with other anticancer agents in cancer combination therapy. Cancer Research, 57, 3375 (1997).

Also, it has recenly been disclosed that CDK inhibitors may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse (U.S. Pat. No. 6,107,305).

Furthermore, it has recently been discovered that cdk5 is involved in the phosphorylation of tau protein, and therefore CDK inhibitors may be useful in the treatment of Alzheimer's disease (J. Biochem., 117, 741–749, 1995).

This body of evidence has led to an intense search for small molecule inhibitors of the cdk family as an approach to cancer chemotherapy. There are no known examples of molecules related to the current invention which describe 5-substituted-indeno [1,2-c]pyrazoles as cdk inhibitors. There is one case describing indeno [1,2-c]pyrazoles having anticancer activity. There are two other examples which describe indeno [1,2-c]pyrazoles having unrelated utilities and structures.

A series of indeno [1,2-c]pyrazoles having anticancer activity are described in JP 60130521 and JP 62099361 with the following generic structure:

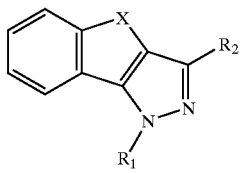

No substitution is claimed on the indenophenyl portion of the molecule and the molecules are not indicated to be cdk inhibitors. In addition, we discovered that substitution at the 5-position was critical for cdk inhibitory activity.

A series of indeno [1,2-c]pyrazoles having herbicidal activity are described in GB 2223946 with the following generic structure:

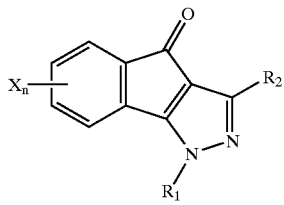

The above compounds differ from the presently claimed invention in $X_n$ is defined as halo, alkyl, haloalkyl, and haloalkoxy; n=0–2. In addition, $R_1$ is defined as acyl and $R_2$ is defined as alkyl or cycloalkyl.

A series of 1-(6'-substituted-4'-methylquinol-2'-yl)-3-methylindeno [1,2-c]pyrazoles having CNS activity are described by Quraishi, Farmaco 44:753–8, 1989 with the following generic structure:

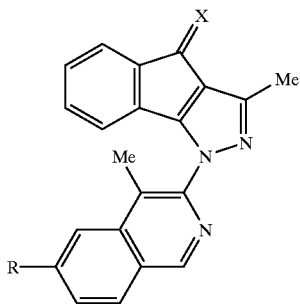

Compounds of this series are not considered to be part of the presently claimed invention.

SUMMARY OF THE INVENTION

The present invention describes a novel class of indeno [1,2-c]pyrazol-4-ones or pharmaceutically acceptable salt forms thereof that are potent inhibitors of the class of enzymes known as cyclin dependent kinases, which relate to the catalytic subunits cdk 1–9 and their regulatory subunits know as cyclins A-H.

It is another object of this invention to provide a novel method of treating proliferative diseases associated with CDK activity by administering a therapeutically effective amount of one of the compounds of the invention or a pharmaceutically acceptable salt form thereof.

It is another object of this invention to provide a novel method of treating cancer associated with CDK activity by administering a therapeutically effective amount of one of the compounds of the invention or a pharmaceutically acceptable salt form thereof.

It is another object of this invention to provide a novel method of treating a proliferative disease, which comprises administering a therapeutically effective combination of one of the compounds of the present invention and one or more other known anti-cancer treatments such as radiation therapy, chemotoxic or chemostatic agents.

These and other objectives have been achieved by the inventors' discovery that compounds of formula (I):

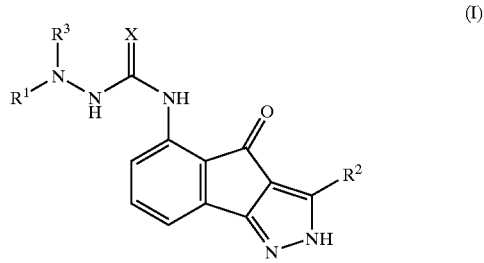

(I)

wherein $R^1$, $R^2$, $R^3$, and X are defined below or pharmaceutically acceptable salts thereof are cyclin dependent kinase inhibitors.

DETAILED DESCRIPTION OF PREFERRED EMBODIMENTS

The invention pertains to novel cyclin dependent kinase inhibitors (cdks) and specifically, but not exclusively, as inhibitors of cdk/cyclin complexes. The inhibitors of this invention are indeno [1,2-c]pyrazol-4-one analogs. Certain analogs were selective for their activity against cdks and their cyclin bound complexes and were less active against other known serine/threonine kinases such as Protein Kinase A (PKA) and Protein Kinase C (PKC).

As described herein, the inhibitors of this invention are capable of inhibiting the cell-cycle machinery and consequently would be useful in modulating cell-cycle progression, which would ultimately control cell growth and differentiation. Such compounds would be useful for treating subjects having disorders associated with excessive cell proliferation, such as the treatment of cancer, psoriasis, immunological disorders involving unwanted leukocyte proliferation, in the treatment of restinosis and other smooth muscle cell disorders, and the like.

The present invention, in a first embodiment, describes novel compounds of formula (I):

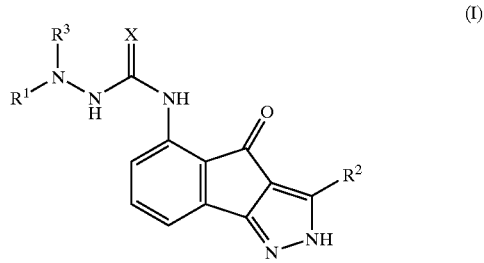

(I)

X is selected from O or S;

$R^1$ is selected from the groups: $C_3$–$C_{10}$ membered carbocycle substituted with 0–5 $R^4$, and 3–10 membered heterocycle substituted with 0–5 $R^5$, provided that if $R^1$ is phenyl then $R^1$ is substituted with 1–5 $R^4$;

$R^2$ is selected from the groups: H, $C_{1-10}$ alkyl substituted with 0–3 $R^6$, $C_{2-10}$ alkenyl substituted with 0–3 $R^6$, $C_{2-10}$ alkynyl substituted with 0–3 $R^6$, —$(CF_2)_mCF_3$, $C_{3-10}$ membered carbocycle substituted with 0–5 $R^4$, and 3–10 membered heterocycle containing from 1–4 heteroatoms selected from O, N, and S and substituted with 0–5 $R^5$;

$R^3$ is selected from the groups: H, $C_{1-4}$ alkyl, $C_{3-6}$ cycloalkyl, or $C_{4-10}$ cycloalkylalkyl;

$R^4$ is independently selected from the groups: halo, —CN, $NO_2$, $C_{1-4}$ alkyl, $C_{1-4}$ haloalkyl, $NR^7R^{7a}$, =O, $OR^7$, $COR^7$, $CO_2R^7$, $CONR^7R^{7a}$, $NHC(O)NR^7R^{7a}$, $NHC(S)NR^7R^{7a}$, $NR^7C(O)OR^{7b}$, $NR^7C(O)R^{7b}$, $SO_2NR^7R^{7a}$, $SO_2R^{7b}$, and 5–10 membered heterocycle containing from 1–4 heteroatoms selected from O, N, and S;

alternatively, when two $R^4$'s are present on adjacent carbon atoms they combine to form —$OCH_2O$—or —$OCH_2CH_2O$—;

$R^5$ is independently selected from the groups: halo, —CN, $NO_2$, $C_{1-4}$ alkyl, $C_{1-4}$ haloalkyl, $NR^7R^{7a}$, $NR^7C(O)OR^{7b}$, $NR^7C(O)R^{7b}$, $OR^7$, $COR^7$, $CO_2R^7$, $CONR^7R^{7a}$, $CON(R^9)$ $[(CH_2)_mR^{10}]$, $CO(CH_2)_mR^{10}$, $NHC(O)NR^7R^{7a}$, $NHC(S)NR^7R^{7a}$, $SO_2NR^7R^{7a}$, and $SO_2R^{7b}$;

$R^6$ is independently selected from the groups: halo, —CN, $NO_2$, $C_{1-4}$ alkyl, $C_{1-4}$ haloalkyl, $NR^7R^{7a}$, $NR^8NR^8R^{8a}$, $NR^7C(O)OR^7$, $NR^7C(O)R^{7b}$, =O, $OR^7$, $COR^7$, $CO_2R^7$, $CONR^7R^{7a}$, $NHC(O)NR^7R^{7a}$, $NHC(S)NR^7R^{7a}$, $SO_2N^7R^{7a}$, $SO_2R^{7b}$, $C_{3-10}$ membered carbocycle substituted with 0–5 $R^4$, and 5–10 membered heterocycle containing from 1–4 heteroatoms selected from O, N, and S, substituted with 0–3 $R^7$;

$R^7$ is independently selected from the groups: H, halo, —CN, $NO_2$, $C_{1-4}$ haloalkyl, $R^8R^{8a}N(CR^9R^{9a})_m$, $NR^8NR^8R^{8a}$, $NR^8C(O)OR^8$, $NR^8C(O)R^8$, =O, $R^8O(CR^9R^{9a})m$, $COR^8$, $CO_2R^8$, $CONR^8R^{8a}$, $NHC(O)NR^8R^{8a}$, $NHC(S)NR^8R^{8a}$, $SO_2NR^8R^{8a}$, $SO_2R^{8b}$, $C_{1-4}$ alkyl, $C_{3-6}$ cycloalkyl, $C_{4-10}$ cycloalkylalkyl, phenyl, and benzyl;

$R^{7a}$ is independently selected from the groups: H, $C_{1-4}$ alkyl, $C_{3-6}$ cycloalkyl, $C_{4-10}$ cycloalkylalkyl, phenyl, and benzyl;

alternatively, $R^7$ and $R^{7a}$, together with the atoms to which they are attached, form a heterocycle having 4–8 atoms in the ring and containing an additional 0–1 N, S, or O atom and substituted with 0–3 $R^{7c}$;

$R^{7b}$ is independently selected from the groups: H, $C_{1-4}$ alkyl, $C_{3-6}$ cycloalkyl, $C_{4-10}$ cycloalkylalkyl, phenyl, and benzyl;

$R^{7c}$ is independently selected from the groups: halo, —CN, $N_3$, $NO_2$, $C_{1-4}$ alkyl, $C_{3-6}$ cycloalkyl, $C_{4-10}$ cycloalkylalkyl, $C_{1-4}$ haloalkyl, $NR^7R^{7b}$, $R^8R^{8a}N(CR^9R^{9a})_m$, =O, $OR^7$, $R^8O(CR^9R^{9a})m$, $COR^7$, $CO_2R^7$, $CONR^7R^{7b}$, $NHC(O)NR^7R^{7b}$, $NHC(S)NR^7R^{7b}$, $NR^7C(O)OR^{7b}$, $NR^7C(O)R^{7b}$, $C(=NR^8)R^{8a}$, $C(=NR^8)NR^{8a}R^{8b}$, $SO_2NR^7R^{7b}$, $SO_2R^{7b}$, and 5–10 membered heterocycle containing from 1–4 heteroatoms selected from O, N, and S;

$R^8$ is independently selected from the groups: H, $C_{1-4}$ alkyl, $C_{3-6}$ cycloalkyl, $C_{4-10}$ cycloalkylalkyl, phenyl and benzyl;

$R^{8a}$ is independently selected from the groups: H, $C_{1-4}$ alkyl, $C_{3-6}$ cycloalkyl, $C_{4-10}$ cycloalkylalkyl, phenyl and benzyl;

alternatively, $R^8$ and $R^{8a}$, together with the atoms to which they are attached, form a heterocycle having 4–8 atoms in the ring and containing an additional 0–1 N, S, or O atom;

$R^{8b}$ is independently selected from the groups: H, $C_{1-4}$ alkyl, $C_{3-6}$ cycloalkyl, $C_{4-10}$ cycloalkylalkyl, phenyl and benzyl;

$R^9$ is idependently selected from the groups: H, $C_{1-4}$ alkyl;

$R^{9a}$ is independently selected from the groups: H, $C_{1-4}$ alkyl;

$R^{10}$ is independently selected from the groups: $NR^7R^{7a}$, $C_{3-10}$ membered carbocycle substituted with 0–3 $R^7$, and 5–10 membered heterocycle containing from 1–4 heteroatoms selected from O, N, and S, substituted with 0–3 $R^7$; and m is independently selected from 0, 1, 2, 3, and 4;

or a pharmaceutically acceptable salt thereof, a pharmaceutically acceptable prodrug form thereof, an N-oxide form thereof, or a stereoisomer thereof.

In a preferred embodiment, the compounds of formula (I) are selected from:

3-(4-piperazinophenyl)-5-((N-methyl-N-(2-pyridinyl) amino)carbamoylamino)indeno [1,2-c]pyrazol-4-one;

3-(4-(4-methylpiperazino)phenyl)-5-((N-methyl-N-(2-pyridinyl)amino)carbamoylamino)indeno [1,2-c]pyrazol-4-one;

3-(4-homopiperazinophenyl)-5-((N-methyl-N-(2-pyridinyl) amino)carbamoylamino)indeno [1,2-c]pyrazol-4-one;

3-(4-(4-methylhomopiperazino)phenyl)-5-((N-methyl-N-(2-pyridinyl)amino)carbamoylamino)indeno [1,2-c] pyrazol-4-one;

3-(4-piperazinophenyl)-5-((N-methyl-N-(4-pyridinyl) amino)carbamoylamino)indeno [1,2-c]pyrazol-4-one;

3-(4-piperazinophenyl)-5-((N-methyl-N-(2-pyrazinyl) amino)carbamoylamino)indeno [1,2-c]pyrazol-4-one;

3-(4-piperazinophenyl)-5-((N-methyl-N-(2-pyrimidinyl) amino)carbamoylamino)indeno [1,2-c]pyrazol-4-one;

3-(4-piperazinophenyl)-5-((N-methyl-N-(2-thiazolyl) amino)carbamoylamino)indeno [1,2-c]pyrazol-4-one;

3-(4-piperazinophenyl)-5-((N-methyl-N-(3-pyridinyl) amino)carbamoylamino)indeno [1,2-c]pyrazol-4-one;

3-(4-(4-methylpiperazino)phenyl)-5-((N-methyl-N-(2-pyrazinyl)amino)carbamoylamino)indeno [1,2-c]pyrazol-4-one;

3-(4-(4-methylpiperazino)phenyl)-5-((N-methyl-N-(2-thiazolyl)amino)carbamoylamino)indeno [1,2-c]pyrazol-4-one;

3-(4-(4-methylpiperazino)phenyl)-5-((N-methyl-N-(3-pyridinyl)amino)carbamoylamino)indeno [1,2-c]pyrazol-4-one;

3-(4-piperazinophenyl)-5-((N-methyl-N-(4-tetrahydropyranyl)amino)carbamoylamino)indeno [1,2-c] pyrazol-4-one;

3-(4-(4-methylpiperazino)phenyl)-5-((N-methyl-N-(4-tetrahydropyranyl)amino)carbamoylamino)-indeno [1,2-c]pyrazol-4-one;

3-(4-(4-ethylpiperazino)phenyl)-5-((N-methyl-N-(4-tetrahydropyranyl)amino)carbamoylamino)indeno [1,2-c] pyrazol-4-one;

3-(4-(4-isopropylpiperazino)phenyl)-5-((N-methyl-N-(4-tetrahydropyranyl)amino)carbamoylamino)-indeno [1,2-c]pyrazol-4-one;

3-(4-(4-piperazinophenyl)-5-((N-methyl-N-cyclohexylamino)carbamoylamino)-indeno [1,2-c] pyrazol-4-one;

3-(4-(4-methylpiperazino)phenyl)-5-((N-methyl-N-cyclohexylamino)carbamoylamino)indeno [1,2-c] pyrazol-4-one;

3-(4-(4-ethylpiperazino)phenyl)-5-((N-methyl-N-cyclohexylamino)carbamoylamino)indeno [1,2-c] pyrazol-4-one;

3-(4-(4-isopropylpiperazino)phenyl)-5-((N-methyl-N-cyclohexylamino)carbamoylamino)-indeno [1,2-c] pyrazol-4-one;

3-(4-piperazinophenyl)-5-((N-methyl-N-(1-methylpiperidin-4-yl)amino)carbamoylamino)indeno [1,2-c]pyrazol-4-one;

3-(4-homopiperazinophenyl)-5-((N-methyl-N-(4-tetrahydropyranyl)amino)carbamoylamino)indeno [1,2-c]pyrazol-4-one;

3-(4-(4-methylhomopiperazino)phenyl)-5-((N-methyl-N-(4-tetrahydropyranyl)amino)carbamoylamino)-indeno [1,2-c]pyrazol-4-one;

3-(4-(4-ethylhomopiperazino)phenyl)-5-((N-methyl-N-(4-tetrahydropyranyl)amino)carbamoylamino)-indeno [1,2-c]pyrazol-4-one;

3-(4-(4-isopropylhomopiperazino)phenyl)-5-((N-methyl-N-(4-tetrahydropyranyl)amino)carbamoylamino)-indeno [1,2-c]pyrazol-4-one;

3-(4-(4-(N,N-dimethylamino)piperidino)phenyl)-5-((N-methyl-N-(4-tetrahydropyranyl)amino) carbamoylamino)-indeno [1,2-c]pyrazol-4-one;

3-(4-(4-pyrrolidinopiperidino)phenyl)-5-((N-methyl-N-(4-tetrahydropyranyl)amino)carbamoylamino)-indeno [1,2-c]pyrazol-4-one;

3-(4-(4-piperidinopiperidino)phenyl)-5-((N-methyl-N-(4-tetrahydropyranyl)amino)carbamoylamino)-indeno [1,2-c]pyrazol-4-one;

3-(2,4-dimethylthiazol-5-yl)-5-((N-methyl-N-(4-tetrahydropyranyl)amino)carbamoylamino)indeno [1,2-c]pyrazol-4-one;

or pharmaceutically acceptable salt form thereof.

Another embodiment of the present invention is a pharmaceutical composition comprising: a pharmaceutically acceptable carrier and a therapeutically effective amount of a compound of formula (I).

Another embodiment of the present invention is a method of treating a proliferative disease associated with CDK activity comprising: administering to a host in need of such treatment a therapeutically effective amount of a compound of formula (I), or a pharmaceutically effective salt form thereof.

Another embodiment of the present invention is a method of treating a cell proliferative disease associated with CDK activity in a patient, comprising administrering to said patient a pharmaceutically effective amount of a compound of formula (I), wherein the proliferative diseases is selected from the group consisting of: Alzheimer's disease, viral infections, auto-immune diseases, fungal disease, cancer, psoriasis, vascular smooth cell proliferation associated with atherosclerosis, pulmonary fibrosis, arthritis glomerulonephritis, neurodegenerative disorders and post-surgical stenosis and restenosis.

Another embodiment of the present invention is a method of treating cancer associated with CDK activity in a patient, comprising administrering to said patient a pharmaceutically effective amount of a compound of formula (I), wherein the cancer is selected from the group consisting of: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Another embodiment of the present invention is a method of treating a disease associated with apoptosis in a patient, comprising administrering to said patient a pharmaceutically effective amount of a compound of formula (I), wherein the disease associated with apoptosis is selected from the group consisting of: cancer, viral infections, autoimmune diseases and neurodegenerative disorder.

Another embodiment of the present invention is a method of inhibiting tumor angiogenesis and metastasis in a patient, comprising administrering to said patient a pharmaceutically effective amount of a compound of formula (I).

Another embodiment of the present invention is a method of treating a disease associated with protein kinase activity in a patient, comprising administrering to said patient a pharmaceutically effective amount of a compound of formula (I), wherein the protein kinase is selected from the group consisting of: e.g. protein kinase C, her2, raf1, MEK1, MAP kinase, EGF receptor, PDGF receptor, IGF receptor, PI3 kinase, weel kinase, Src, and Abl.

Another embodiment of the present invention is a method of modulating the level of cellular RNA and DNA synthesis in a patient, comprising administering to said patient a CDK inhibitory effective amount of a compound of formula (I).

Another embodiment of the present invention is a method of treating viral infections in a patient, comprising administering to said patient a CDK inhibitory effective amount of a compound of formula (I), wherein the viral infections is selected from the group consiting of HIV, human papilloma virus, herpesvirus, poxvirus, Epstein-Barr virus, Sindbis virus and adenovirus.

Another embodiment of the present invention is a method of chemopreventing cancer in a patient, comprising administering to said patient a CDK inhibitory effective amount of a compound of formula (I).

Another embodiment of the present invention is a method of inhibiting CDK activity comprising combining an effective amount of the compound of formula (I) with a composition containing CDK.

Another embodiment of the present invention is a method of treating cancer associated with CDK activity in a patient, comprising administrering to said patient a pharmaceutically effective amount of a compound of formula (I) in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methoxtrexate.

Another embodiment of the present invention is a method treating proliferative diseases associated with CDK activity, in a patient, comprising administrering to said patient a pharmaceutically effective amount of a compound of formula (I), in combination (administered together or sequentially) with known anti-proliferating agents selected from the group consisting of:, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPT-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, and estramustine, hydroxyurea.

Another embodiment of the present invention is a method of inhibiting CDK1 activity, comprising adminsitering to a patient in need thereof an effective CDK1 inhibitory amount of a compound according to claim 1, or a pharmaceutically acceptable salt or prodrug form thereof.

Another embodiment of the present invention is a method of inhibiting CDK2 activity, comprising adminsitering to a patient in need thereof an effective CDK2 inhibitory amount of a compound according to claim 1, or a pharmaceutically acceptable salt or prodrug form thereof.

Another embodiment of the present invention is a method of inhibiting CDK3 activity, comprising adminsitering to a patient in need thereof an effective CDK3 inhibitory amount of a compound according to claim 1, or a pharmaceutically acceptable salt or prodrug form thereof.

Another embodiment of the present invention is a method of inhibiting CDK4 activity, comprising adminsitering to a patient in need thereof an effective CDK4 inhibitory amount of a compound according to claim 1, or a pharmaceutically acceptable salt or prodrug form thereof.

Another embodiment of the present invention is a method of inhibiting CDK5 activity, comprising adminsitering to a patient in need thereof an effective CDK5 inhibitory amount of a compound according to claim 1, or a pharmaceutically acceptable salt or prodrug form thereof.

Another embodiment of the present invention is a method of inhibiting CDK6 activity, comprising adminsitering to a patient in need thereof an effective CDK6 inhibitory amount of a compound according to claim 1, or a pharmaceutically acceptable salt or prodrug form thereof.

Another embodiment of the present invention is a method of inhibiting CDK7 activity, comprising adminsitering to a patient in need thereof an effective CDK7 inhibitory amount of a compound according to claim 1, or a pharmaceutically acceptable salt or prodrug form thereof.

Another embodiment of the present invention is a method of inhibiting CDK8 activity, comprising adminsitering to a patient in need thereof an effective CDK8 inhibitory amount of a compound according to claim 1, or a pharmaceutically acceptable salt or prodrug form thereof.

Another embodiment of the present invention is a method of inhibiting CDK9 activity, comprising adminsitering to a patient in need thereof an effective CDK9 inhibitory amount of a compound according to claim 1, or a pharmaceutically acceptable salt or prodrug form thereof.

It is a further object of the invention to provide a pharmaceutical kit for treating proliferative diseases associated with CDK activity, said kit comprising a plurality of separate containers, wherein at least one of said containers contains a compound of formula (I), and at least another of said containers contains one or more compounds selected from the group consisting of altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPT-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, and estramustine, hydroxyurea, and said containers optionally contain a pharmaceutical carrier, which kit may be effectively utilized for carrying out combination therapies according to the invention.

It is a further object of the invention to provide a method of treating a patient having a disorder associated with excessive cell proliferation, comprising administering to the patient a therapeutically effective amount of a compound of formula (I), such that the excessive cell proliferation in the patient is reduced.

It is appreciated that certain feactures of the invention, which are, for clarity, described in the context of separate embodiments, may also be provided in combination in a single embodiment. Conversely, various feactures of the invention which are, for brevity, described in the context of a single embodiment, may also be provided seperately or in any suitable subcombination.

DETAILED DESCRIPTION OF THE INVENTION

As used above, and throughout the description of the invention, the following terms, unless otherwise indicated, shall be understood to have the following meanings:

Definitions

As used herein, the following terms and expressions have the indicated meanings.

The term "compounds of the invention", and equivalent expressions, are meant to embrace compounds of the invention as herein before described i.e. compounds of formula (I), which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "effective amount" means an amount of a compound/composition according to the present invention effective in producing the desired therapeutic effect.

The term "amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, and the like.

The term "acid labile amine protecting group" means an amine protecting group as defined above which is readily removed by treatment with acid while remaining relatively stable to other reagents. A preferred acid labile amine protecting group is tert-butoxycarbonyl (BOC).

The term "hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

The term "hydrogenation labile acid protecting group" means an acid protecting group as defined above which is readily removed by hydrogenation while remaining relatively stable to other reagents. A preferred hydrogenation labile acid protecting group is benzyl.

The term "analogue" means a compound which comprises a chemically modified form of a specific compound or class thereof, and which maintains the pharmaceutical and/or pharmacological activities characteristic of said compound or class.

The term "patient" includes both human and other mammals.

The term "pharmaceutical composition" means a composition comprising a compound of formula (I) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

The term "solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkythio, thioester, sulfonyl, nitro, heterocyclo, aryl or heteroaryl. It will also be understood by those skilled in the art that the substituted moieties themselves can be substituted as well when appropriate.

The terms "halo" or "halogen" as used herein refer to fluoro, chloro, bromo and iodo.

As used herein, "carbocycle" or "carbocyclic residue" is intended to mean cycloalkyl, cycloalkenyl, or haryl groups as described herein, Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

"Cycloalkyl" means a non-aromatic mono- or multicyclic ring system of about 3 to about 10 carbon atoms, preferably of about 5 to about 10 carbon atoms. Preferred ring sizes of monocyclic ring systems include about 5 to about 6 ring atoms. The cycloalkyl is optionally substituted with one or more substituents which may be the same or different, and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred ring sizes monocyclic ring systems include about 5 to about 6 ring atoms. The cycloalkenyl is optionally substituted with one or more substituents which may be the same or different, and are as defined herein. Exemplary monocyclic cycloalkenyl include cyclopentenyl, cyclohexenyl, cycloheptenyl, and the like. An exemplary multicyclic cycloalkenyl is norbornylenyl.

"Aryl" means an aromatic monocyclic or multicyclic ring system of about 5 to about 10 carbon atoms, preferably of about 5 to about 6 carbon atoms. The aryl is optionally substituted with one or more substituents which may be the same or different, and are as defined herein. Exemplary aryl groups include phenyl or naphthyl, or phenyl substituted or naphthyl substituted.

"Cycloalkylalkyl" means a cycloalkyl-alkyl group wherein the cycloalkyl and alkyl are as herein described. Preferred cycloalkylalkyl contain a lower alkyl moiety. An exemplary cycloalkylalkyl group is cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

As used herein, the term "heterocycle" or "heterocyclic system" is intended to mean a heterocyclyl, heterocyclenyl, or heteroaryl groups as described herein, which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

"Heterocyclenyl" means a non-aromatic monocyclic or multicyclic hydrocarbon ring system of about 3 to about 10 atoms, preferably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferred ring sizes of rings of the ring system include about 5 to about 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or $R^4$ substitents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxa-heterocyclenyl groups include 3,4-dihydro-2H-pyran, dihydrofuranyl, and fluorodihydrofuranyl. Preferred is dihydrofuranyl. An exemplary multicyclic oxaheterocyclenyl group is 7-oxabicyclo[2.2.1]heptenyl. Preferred monocyclic thiaheterocycleny rings include dihydrothiophenyl and dihydrothiopyranyl; more preferred is dihydrothiophenyl.

"Heterocyclyl" means a non-aromatic saturated monocyclic or multicyclic ring system of about 3 to about 10 carbon atoms, preferably about 4 to about 8 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more $R^4$ substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" means an aromatic monocyclic or multicyclic ring system of about 5 to about 10 atoms, in which one or more of the atoms in the ring system is/are hetero element(s) other than carbon, for example nitrogen, oxygen or sulfur. Preferred ring sizes of rings of the ring system include about 5 to about 6 ring atoms. The "heteroaryl" may also be substituted by one or more R4 subsituents which may be the same or different, and are as defined herein. The designation of the aza, oxa or thia as a prefix before heteroaryl define that at least a nitrogen, oxygen or sulfur atom is present respectively as a ring atom. A nitrogen atom of an heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo [1,2-a]pyridine, imidazo [2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3, 4-thiadiazolyl, thiazolyl, thienyl and triazolyl.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "Pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. The transformation in vivo may be, for example, as the result of some metabolic process, such as chemical or enzymatic hydrolysis of a carboxylic, phosphoric or sulphate ester, or reduction or oxidation of a susceptible functionality. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p.309–396, 1985; A Textbook of Drug Design and Development, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

The term "Treating" refers to:
(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

Preparation of Compounds of the Invention

It will be apparent to those skilled in the art that certain compounds of formula (I) can exhibit isomerism, for example geometrical isomerism, e.g., E or Z isomerism, and optical isomerism, e.g., R or S configurations. Geometrical isomers include the cis and trans forms of compounds of the invention having alkenyl moieties. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on CDK inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on CDK inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are more likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

Preferred methods of synthesizing the compounds of the invention include, but are not limited to, those methods described below. Each of the references cited below are hereby incorporated herein by reference.

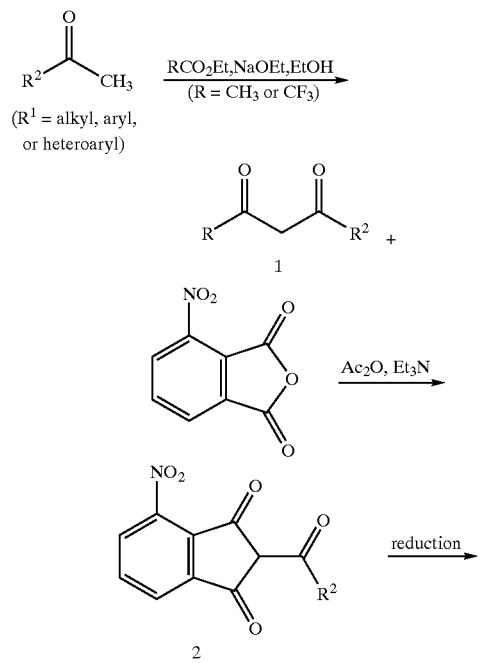

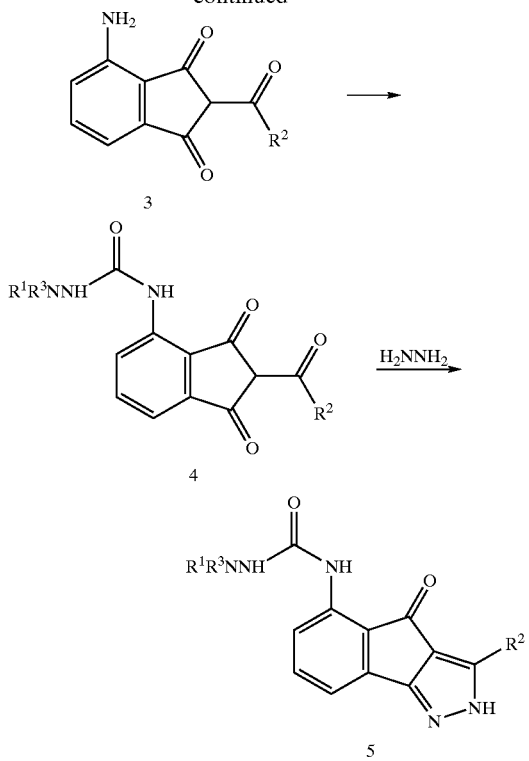

An approach to preparing indeno [1,2-c]pyrazol-4-ones is presented in Scheme 1 and can be used to prepare compounds of the present invention. This method employs the condensation of a 1,3-diketone 1 with 3-nitrophthalic anhydride as described in Rotberg and Oshkaya, Zh. Organ. Khim. 8:84–87, 1972; Zh. Organ. Khim. 9:2548–2550, 1973, the contents of which are hereby incorporated herein by reference. The 1,3-diketones, when not commercially available can be readily prepared by one skilled in the art by the acetylation or trifluoroacetylation of the requisite methyl ketone, $R^2COCH_3$. Reduction of the nitro derivative 2 to the aniline 3 can be accomplished in a variety of ways including catalyic hydrogenation, treatment with zinc or iron under acidic conditions, or treatment with other reducing agents such as sodium dithionite or stannous chloride. The aniline 3 can be converted to the corresponding semicarbazide by a variety of methods described below. The triketone 4 then was treated with hydrazine at elevated temperature in an appropriate solvent to give the indeno [1,2-c]pyrazol-4-one ring system.

The semicarbazides 4 (X=O) of Scheme 1 can be prepared by treating the aniline 3 with an aminoisocyanate (RR'NNCO). These reagents are generated in situ employing a precursor, such as an O-phenylcarbamate (RR'NNHCO$_2$Ph), in the presense of base. Alternatively, the semicarbazides can be prepared by treatment of the aniline intermediates above with phenyl chloroformate in the presense of base to give an intermediate phenyl carbamate, followed by exposure of the phenyl carbamate to a hydrazine at elevated temperatures in an appropriate solvent. The thiosemicarbazides (X=S) of this invention can be prepared as described above by treating the aniline intermediates with phenyl thionochloroformate, followed by exposure of the resulting phenyl thiocarbamate to the appropriate hydrazine derivative. The thiosemicarbazides of this invention can also be prepared from the corresponding semicarbazides by

SCHEME 2

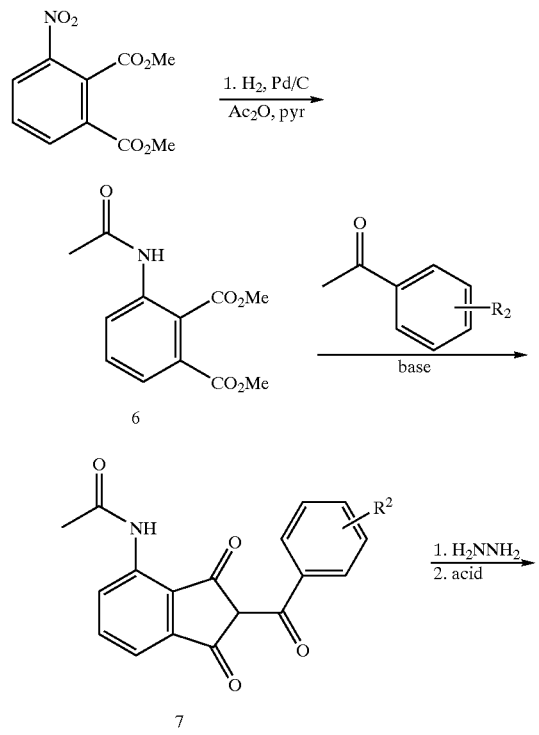

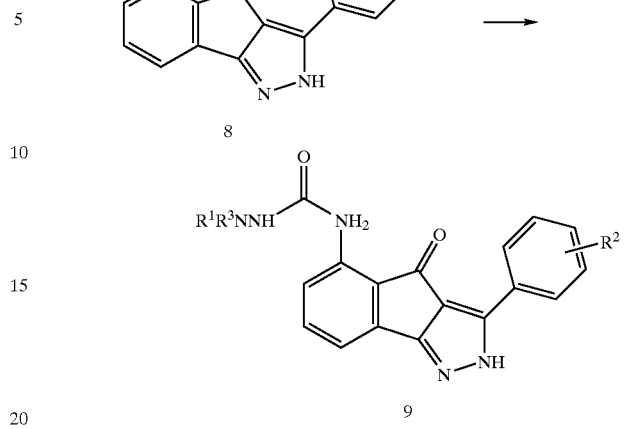

Another approach to preparing indeno [1,2-c]pyrazol-4-ones is presented in Scheme 2 and can be used to prepare compounds of the present invention. The nitro group of dimethyl 3-nitrophthalate was reduced to the amine using catalytic hydrogenation. The aniline was acylated using acetic anhydride and pyridine as a base. A mixture of the resulting acetamide 6 and an acetophenone were treated with a strong base in an appropriate solvent at elevated temperature to give the desired triketone 7. The triketone was treated with hydrazine at elevated temperature in an appropriate solvent to give the indeno [1,2-c]pyrazol-4-one ring system. The amide was deacetylated by heating with a strong acid in an appropriate solvent to give aniline 8. This aniline was converted to the semicarbazide 9 employing one of the methods described above.

SCHEME 3

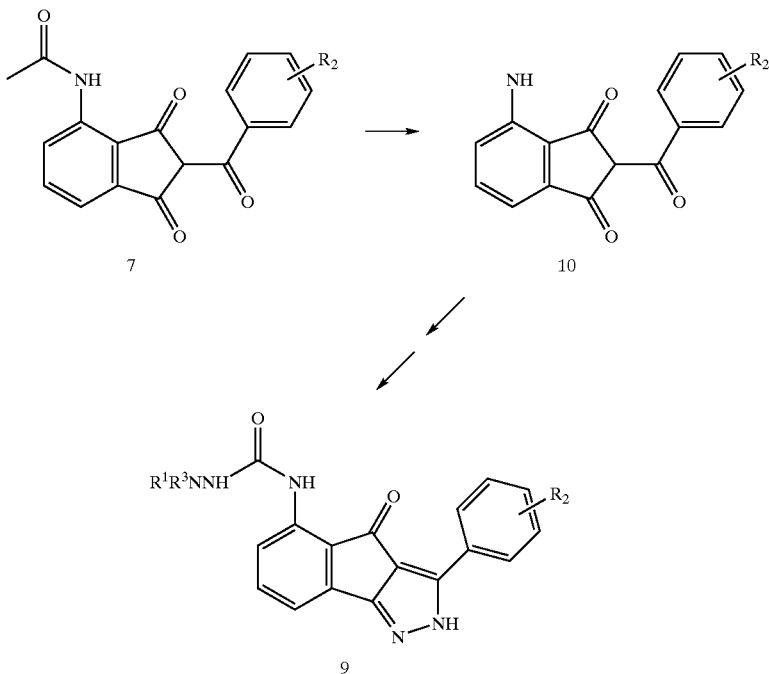

A third method for making compounds of the present invention is shown in Scheme 3. The intermediate triketone 7, prepared in Scheme 2, can be deacetylated with strong acid. Subsequently, aniline 10 can be converted to the indeno [1,2-c]pyrazol-4-ones using the same conditions described previously in Scheme 1.

Many of the compounds of this invention are synthesized from the indeno [1,2-c]pyrazol-4-ones prepared in Schemes 1–3 by the further synthetic elaboration of the $R^1$ and $R^2$ groups. As required the pyrazole ring can be protected by a wide range of protecting groups known to one skilled in the art with the selection of a protecting depending on the chemistry to be employed.

Other features of the invention will become apparent during the following descriptions of exemplary embodiments which are given for illustration of the invention and are not intended to be limiting thereof.

EXAMPLES

Abbreviations used in the Examples are defined as follows: "° C." for degrees Celsius, "CIMS" for chemical ionization mass spectroscopy, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "p-TsOH" for para-toluenesulphonic acid, "DMF" for dimethylformamide, and "TFA" for trifluoroacetic acid.

Example 1

Preparation of 3-(4-piperazinophenyl)-5-((N-methyl-N-(2-pyridinyl)amino)carbamoylamino) indeno [1,2-c]pyrazol-4-one

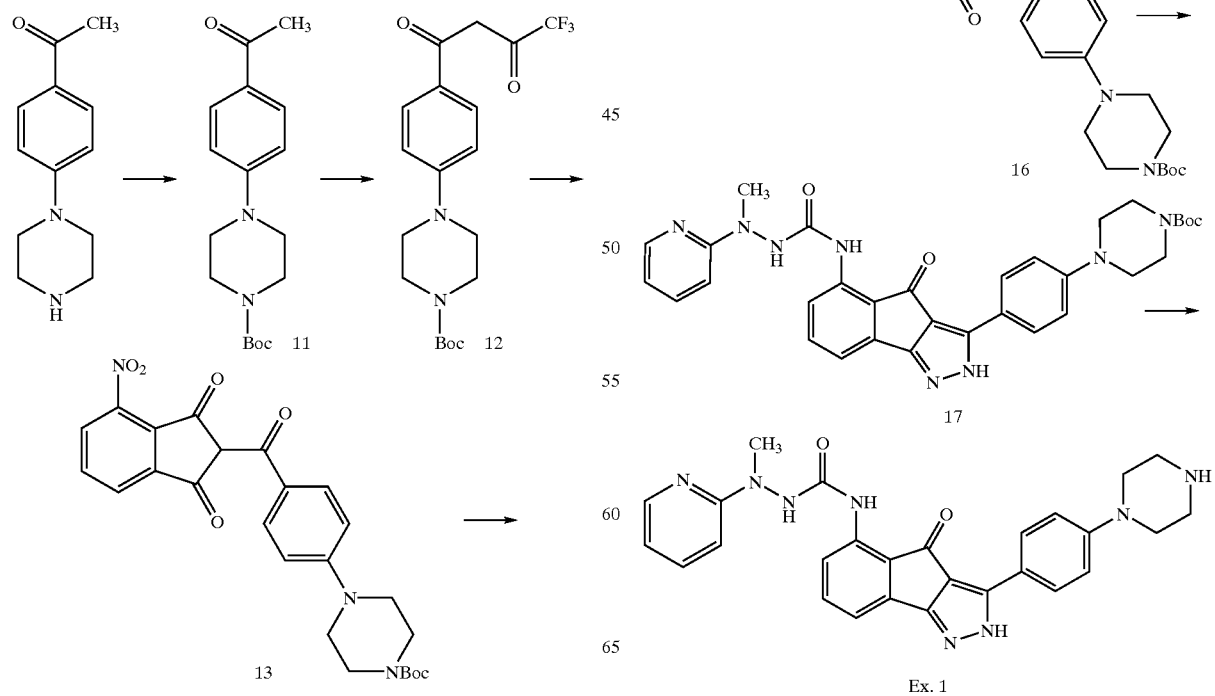

Step 1. Synthesis of 11

To a suspension of 139 g (680 mmol) of 4-piperazinoacetophenone in 700 mL of tetrahydrofuran at 25° C. was added slowly over 20 min. a solution of 157 g (720 mmol) of di-tert-butyl dicarbonate in 300 mL of tetrahydrofuran. The resulting mixture was refluxed for 15h. After cooling the mixture was filtered, and the filtrate was concentrated under vacuum to provide an off-white solid. This crude product was recrystallized from diethyl ether/hexane to afford 192 g of the 11 as a white solid. NMR (CDCl$_3$) δ 7.89 (d, 2H, J=9 Hz), 6.87 (d, 2H, J=9 Hz), 3.59 (m, 4H), 3.33 (m, 4H), 2.53 (s, 3H), 1.49 (s, 9H).

Step 2. Synthesis of 12 from 11

To a solution of 192 g (630 mmol) of 11 and 90 mL (750 mmol) of ethyl trifluoroacetate in 1000 mL of tetrahydrofuran at 25° C. was added slowly over 15 min. 280 mL (750 mmol) of 21% sodium ethoxide in ethanol, and the resulting solution then was stirred at 25° C. for 16 h. The reaction mixture was diluted with 500 mL of water, and to this mixture was added 45 mL of acetic acid. The resulting precipitate was recovered by filtration. The solids were washed with diethyl ether/hexane and dried to furnish 236 g of 12 as an orange solid. NMR (CDCl$_3$) δ 7.87 (d, 2 H, J=9 Hz), 6.87 (d, 2 H, J=9 Hz), 6.45 (s, 1H), 3.60 (m, 4H), 3.41 (m, 4H), 1.48 (s, 9H).

Step 3. Synthesis of 13 from 12

A suspension of 117 g (610 mmol) of 3-nitrophthalic anhydride in 560 mL of acetic anhydride was heated until the mixture became homogeneous, and the solution then was allowed to cool to room temperature. To this solution was added 236 g (590 mmol) of 12. The resulting mixture was cooled to 0° C., and 165 mL (1200 mmol) of triethylamine was added slowly over 10 min. The mixture was allowed to warm to 25° C., was stirred at 25° C. for 1 h, and then was heated to 65° C. for 0.5 h. After cooling to room temperature, the reaction mixture was poured into a well-stirred solution of 1200 mL of 1.0 N hydrochloric acid and 2000 mL of ethanol. The resulting precipitate was recovered by filtration, washed with ethanol, and dried to provide 140 g of 13 as an orange solid. NMR (acetone-d$_6$) δ 8.34 (d, 2H, J=9 Hz), 8.05 (m, 3H), 7.07 (d, 2H, J=9 Hz), 3.59 (br s, 8H), 1.48 (s, 9H).

Step 4. Synthesis of 14 from 13

To a solution of 12.00 g (25 mmol) of 13 in 500 mL of ethanol and 50 mL of conc. ammonium hydroxide at 25° C. was added 500 mL of water, followed by 15.3 g (88 mmol) of sodium dithionite. The resulting mixture was stirred at 25° C. for 16 h. The reaction mixture was filtered, and the filtrate was reduced to ~½ the original volume under vacuum. This solution was adjusted to pH 3 employing hydrochloric acid and then extracted with ethyl acetate. The combined extracts were washed with water and brine, dried over anhyd. sodium sulfate, filtered, and concentrated. The resulting solids were recrystallized from ethanol/water to provide 8.40 g of 14 as a green solid. NMR (DMSO-d$_6$) δ 8.20 (d, 2H, J=9 Hz), 7.44 (t, 1H, J=8 Hz), 7.02 (d, 2H, J=9 Hz), 6.96 (d, 1H, J=8 Hz), 6.91 (d, 1H, J=8 Hz), 6.70 (br s, 2H), 3.46 (br s, 8H), 1.43 (s, 9H).

Step 4. Synthesis of 15 from 14

To a mixture of 1.35 g (3 mmol) of 14, 1.65 g (12 mmol) of powdered potassium carbonate, and 50 mL of acetone at 25° C. was added 0.45 mL (3.6 mmol) of phenyl chloroformate, and the reaction mixture then was stirred at 25° C. for 15 h. The mixture was diluted with 200 mL of water, adjusted to pH 3 employing hydrochloric acid, and extracted with ethyl acetate. The combined extracts were washed with water and brine, dried over anhydrous sodium sulfate, and concentrated. The resulting crude solids were recrystallized from 95% aqueous ethanol to afford 0.95 g of 15 as an orange solid. NMR (CDCl$_3$) δ 10.32 (br s, 1H), 8.52 (d, 1H, J=8.5 Hz), 8.30 (d, 2H, J=8.5 Hz), 7.65 (t, 1H, J=8.5 Hz), 7.48 (m, 3H), 7.23 (m, 3H), 6.92 (d, 2H, J=8.5 Hz), 3.60 (m, 4H), 3.45 (m, 4H), 1.49 (s, 9H).

Step 5. Synthesis of 16 from 15

A solution of 0.57 g (1 mmol) of 15, 0.25 g (2 mmol) of 1-methyl-1-(2-pyridinyl)hydrazine [prepared from 2-bromopyridine and 1-methylhyrazine by the procedure of M. A. Baldo, et al., Synthesis (1987), 720–3], 0.37 g (3 mmol) of 4-dimethylaminopyridine, and 15 mL of DMSO was stirred at 90° C. for 4 h. After cooling to ambient temperature the mixture was diluted with 60 mL of water, adjusted to pH 5 employing hydrochloric acid, and extracted with ethyl acetate. The combined extracts were washed with water and brine, dried over anhydrous sodium sulfate, and concentrated under vacuum to provide the crude product. This material was employed in the subsequent reaction without further purification.

Step 6. Synthesis of 17 from 16

A mixture of 16, 0.10 mL (2 mmol) of hydrazine hydrate, 0.014 g (0.2 mmol) of hydrazine hydrochloride, and 15 mL of ethanol was heated at reflux for 20 h. While still at reflux the mixture was diluted by the dropwise addition of 10 mL of water. After the mixture had cooled to ambient temperature, the precipitate was recovered by filtration, washed with aqueous ethanol, and dried under vacuum to provide 0.12 g of 17 as a yellow solid.

Step 7. Synthesis of Ex. 1 from 16

A solution of 0.12 g of 17 in 10 mL of trifluoroacetic acid was stirred at 25° C. for 2 h. The excess trifluoroacetic acid was removed under vacuum, and the resulting solids were purified by preparative HPLC to afford 0.050 g of the product as its TFA-salt. ESI-MS m/e calc'd for C$_{27}$H$_{27}$N$_8$O$_2$: 495.2257, found: 495.2262.

Example 2

Preparation of 3-(4-(4-methylpiperazino)phenyl)-5-((N-methyl-N-(2-pyridinyl)amino)carbamoylamino) indeno [1,2-c]pyrazol-4-one

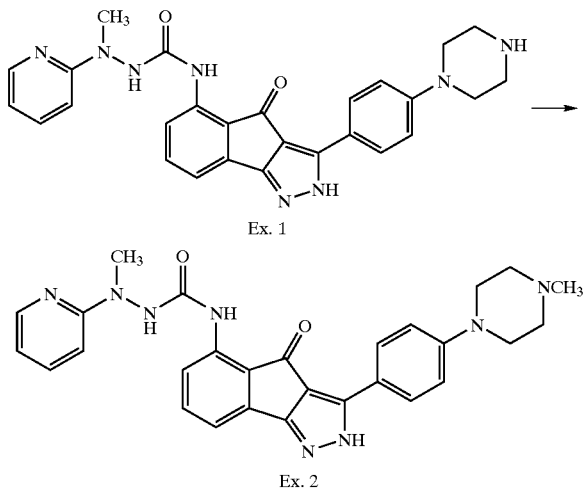

To a solution of Ex. 1 (0.21 g, 0.29 mmol) in 10 mL of methanol and 2 mL of water at 25° C. was added sequentially 37% aqueous formaldehyde (0.45 g, 5.8 mmol), sodium cyanoborohydride (0.18 g, 2.9 mmol), and 4 drops of acetic acid. The resulting solution was stirred at 25° C. for 16 h. The mixture was diluted with water. It then was made acidic (~pH 1) with conc. hydrochloric acid and stirred for 10 min. The solution next was made basic (~pH 13) with 50% aqueous sodium hydroxide and finally adjusted to pH 10 with 1 N hydrochloric acid. The precipitate was recovered by filtration, washed with water, and dried. To sloid was dissolved in excess trifluoroacetic acid, and the solution was diluted with ethanol. The resulting precipitate was recovered by filtration, washed with ethanol, and dried under vacuum to afford 0.075 g of the yellow product as its TFA-salt. ESI-MS m/e calc'd for $C_{28}H_{29}N_8O_2$: 509.2413, found: 509.2412.

Example 3

Preparation of 3-(4-homopiperazinophenyl)-5-((N-methyl-N-(2-pyridinyl)amino)carbamoylamino) indeno [1,2-c]pyrazol-4-one

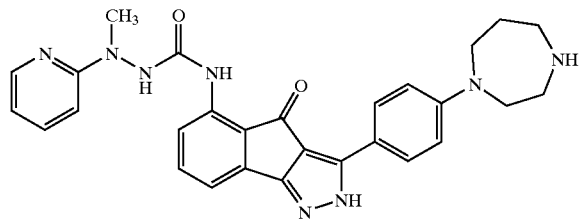

Prepared in a manner as described for example 1 employing 4-(4-t-butoxycarbonylhomopiperazino)acetophenone as starting material. ESI-MS m/e calc'd for $C_{28}H_{29}N_8O_2$: 509.2413, found: 509.2415.

Example 4

Preparation of 3-(4-(4-methylhomopiperazino) phenyl)-5-((N-methyl-N-(2-pyridinyl)amino) carbamoylamino)indeno [1,2-c]pyrazol-4-one

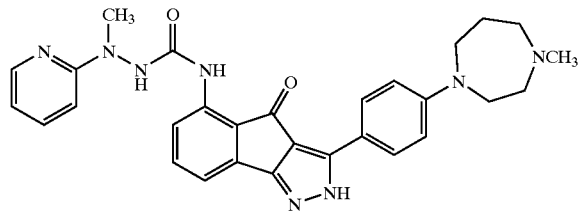

Prepared in a manner as described for example 2 employing example 3 as starting material. ESI-MS m/e calc'd for $C_{29}H_{31}N_8O_2$: 523.2570, found: 523.2599.

Example 5

Preparation of 3-(4-piperazinophenyl)-5-((N-methyl-N-(4-pyridinyl)amino)carbamoylamino) indeno [1,2-c]pyrazol-4-one

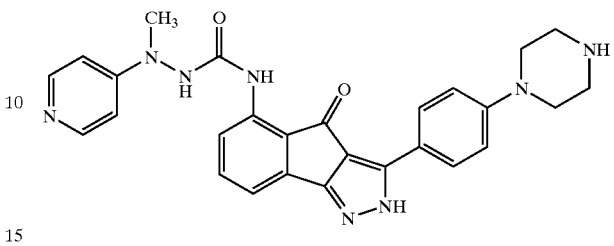

Prepared in a manner as described for example 1 employing 14 and 1-methyl-1-(4-pyridinyl)hydrazine [prepared from 4-bromopyridine hydrochloride and 1-methylhyrazine by the procedure of M. A. Baldo, et al., Synthesis (1987), 720–3] as starting materials. ESI-MS m/e calc'd for $C_{27}H_{27}N_8O_2$: 495.2257, found: 495.2261.

Example 6

Preparation of 3-(4-piperazinophenyl)-5-((N-methyl-N-(2-pyrazinyl)amino)carbamoylamino) indeno [1,2-c]pyrazol-4-one

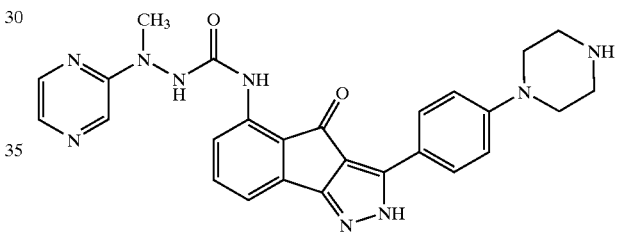

Prepared in a manner as described for example 1 employing 14 and 1-methyl-1-(2-pyrazinyl)hydrazine [prepared from 2-bromopyrazine and 1-methylhyrazine by the procedure of M. A. Baldo, et al., Synthesis (1987), 720–3] as starting materials. ESI-MS m/e calc'd for $C_{26}H_{26}N_9O_2$: 496.2210, found: 496.2208.

Example 7

Preparation of 3-(4-piperazinophenyl)-5-((N-methyl-N-(2-pyrimidinyl)amino)carbamoylamino) indeno [1,2-c]pyrazol-4-one

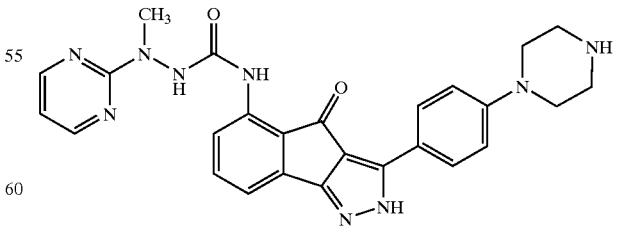

Prepared in a manner as described for example 1 employing 14 and 1-methyl-1-(2-pyrimidinyl)hydrazine [prepared from 2-bromopyrimidine and 1-methylhyrazine by the procedure of M. A. Baldo, et al., Synthesis (1987), 720–3] as starting materials. ESI-MS m/e calc'd for $C_{26}H_{26}N_9O_2$: 496.2210, found: 496.2218.

Example 8

Preparation of 3-(4-piperazinophenyl)-5-((N-methyl-N-(2-thiazolyl)amino)carbamoylamino)indeno [1,2-c]pyrazol-4-one

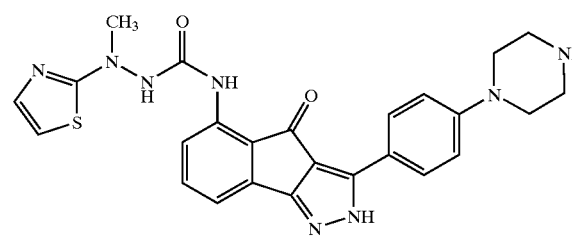

Prepared in a manner as described for example 1 employing 14 and 1-methyl-1-(2-thiazolyl)hydrazine [prepared from 2-bromothiazole and 1-methylhyrazine by the procedure of M. A. Baldo, et al., Synthesis (1987), 720–3] as starting materials. ESI-MS m/e calc'd for $C_{25}H_{25}N_8O_2S$: 501.1821, found: 501.1796.

Example 9

Preparation of 3-(4-piperazinophenyl)-5-((N-methyl-N-(3-pyridinyl)amino)carbamoylamino)indeno [1,2-c]pyrazol-4-one

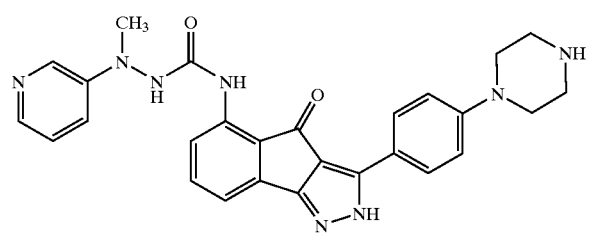

Prepared in a manner as described for example 1 employing 14 and 1-methyl-1-(3-pyridinyl)hydrazine [prepared from 3-(methylamino)pyridine by treatment with tert-butylnitrite, followed by reduction of the intermediate nitrosamine with lithium aluminum hydride] as starting materials. ESI-MS m/e calc'd for $C_{27}H_{27}N_8O_2$: 495.2257, found: 495.2260.

Example 10

Preparation of 3-(4-(4-methylpiperazino)phenyl)-5-((N-methyl-N-(2-pyrazinyl)amino)carbamoylamino)indeno [1,2-c]pyrazol-4-one

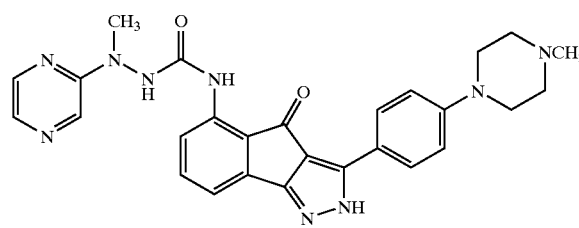

Prepared in a manner as described for example 2 employing example 6 as starting material. ESI-MS m/e calc'd for $C_{27}H_{28}N_9O_2$: 510.2366, found: 510.2358.

Example 11

Preparation of 3-(4-(4-methylpiperazino)phenyl)-5-((N-methyl-N-(2-thiazolyl)amino)carbamoylamino)indeno [1,2-c]pyrazol-4-one

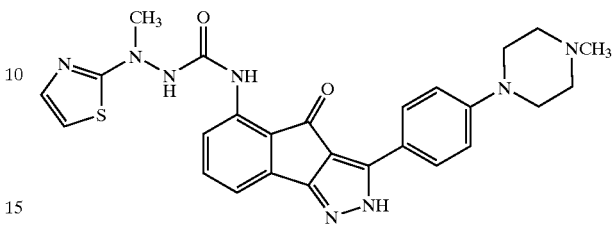

Prepared in a manner as described for example 2 employing example 8 as starting material. ESI-MS m/e calc'd for $C_{26}H_{27}N_8O_2S$: 515.1977, found: 515.2007.

Example 12

Preparation of 3-(4-(4-methylpiperazino)phenyl)-5-((N-methyl-N-(3-pyridinyl)amino)carbamoylamino)indeno [1,2-c]pyrazol-4-one

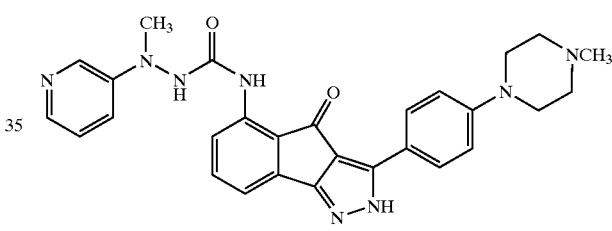

Prepared in a manner as described for example 2 employing example 9 as starting material. ESI-MS m/e calc'd for $C_{28}H_{29}N_8O_2$: 509.2413, found: 509.2421.

Example 13

Preparation of 3-(4-piperazinophenyl)-5-((N-methyl-N-(4-tetrahydropyranyl)amino)carbamoylamino)indeno [1,2-c]pyrazol-4-one

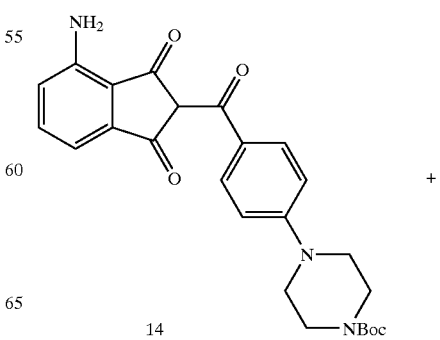

14

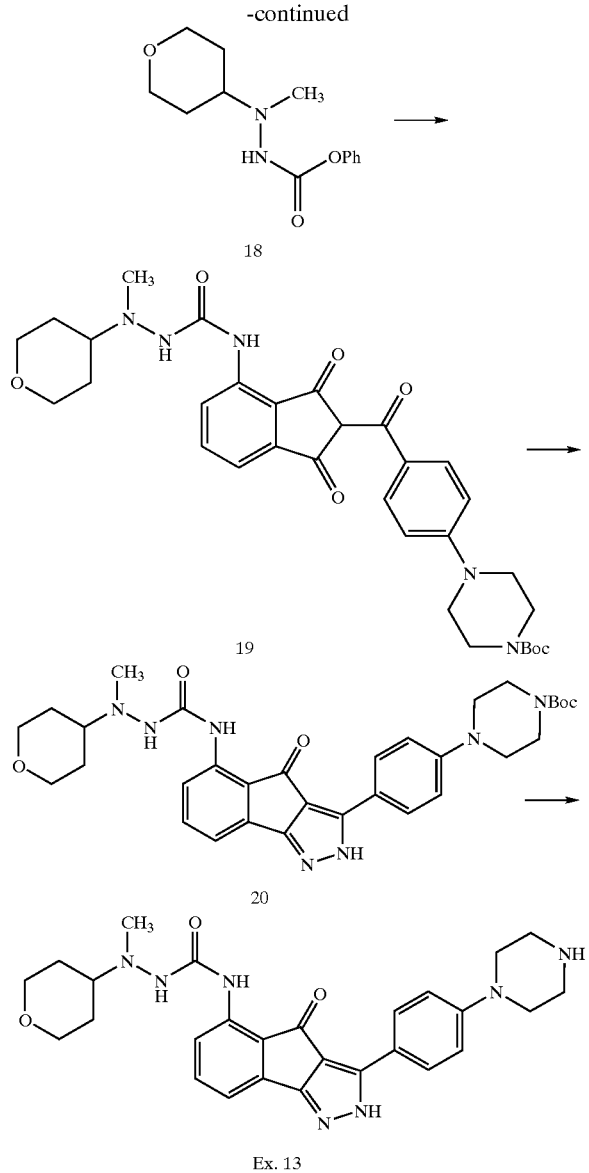

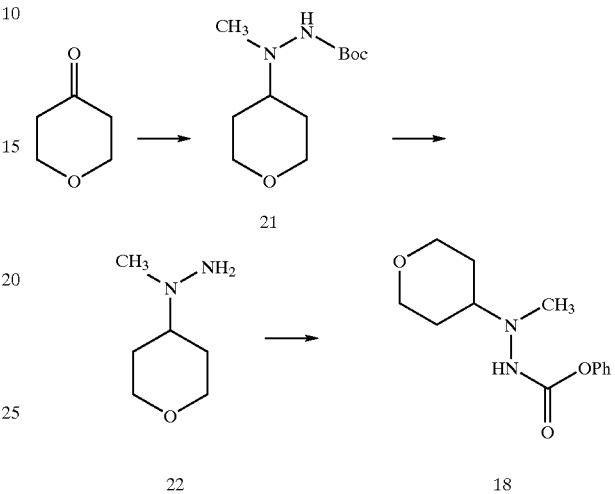

Step 1. Synthesis of 19 from 14 and 18

A solution of 4.50 g (10 mmol) of 14, 5.00 g (20 mmol) of 18 (prepared as described below), 3.68 g (30 mmol) of 4-dimethylaminopyridine, and 80 mL of DMSO was stirred at 90° C. for 2.5 h. After cooling to room temperature the reaction mixture was poured into a well-stirred solution of 80 mL of ethanol and 30 mL of 1N hydrochloric acid. The resulting solution was diluted further by the slow addition of 120 mL of water. A precipitate formed. It was recovered by filtration, washed with 50% aqueous ethanol, and dried to provide 4.00 g of 19 as an orange solid. ESI-MS m/e: 604 (M−H)⁻.

Step 2. Synthesis of 20 from 19

A mixture of 4.00 g (6.6 mmol) of 19, 0.64 mL (13.2 mmol) of hydrazine monohydrate, 0.090 g (1.32 mmol) of hydrazine hydrochloride, and 130 mL of ethanol was refluxed for 18 h. While still at reflux the solution was diluted by the dropwise addition of 30 mL of water. The mixture then was allowed to cool to room temperature. The resulting precipitate was recovered by filtration, washed with 80% aqueous ethanol, and dried to afford 1.88 g of 20 as a yellow solid. ESI-MS m/e: 602 (M+H)⁺.

Step 3. Synthesis of Ex. 13 from 20

A solution of 20 (0.60 g, 1.0 mmol) in 20 mL of trifluoroacetic acid was stirred at 25° C. for 2 h. The reaction mixture was concentrated under vacuum, and the residue was recrystallized from ethanol to provide 0.55 g of the yellow product as its TFA-salt. ESI-MS m/e calc'd for $C_{27}H_{32}N_7O_3$: 502.2566, found: 502.2583.

Preparation of 18

Step 1. Synthesis of 21

A solution of 20.78 g (208 mmol) of tetrahydropyran-4-one and 27.43 g (208 mmol) of t-butyl carbazate in 250 mL of methanol was heated at reflux for 6 h. After cooling to ambient temperature the solution was diluted with an additional 750 mL of methanol. To this solution at 0° C. was added 39.00 g (622 mmol) of sodium cyanoborohydride and 13.70 mL (228 mmol) of acetic acid. The resulting mixture was stirred at 25° C. for 16 h. To the reaction mixture at 0° C. was added 60 mL of 37% aqueous formaldehyde solution. The mixture then was stirred at 25° C. for 5 h. The mixture was concentrated under vacuum, made basic by the addition of 400 mL of 1N aqueous sodium hydroxide, and extracted with methylene chloride. The combined extracts were washed with brine, dried over anhydrous sodium sulfate, filtered, and concentrated. The resulting solids were washed with diethyl ether/hexane and the dried to afford 44.50 g of 21 as a white solid. NMR (CDCl₃) δ 5.75 (br s, 1H), 4.01 (m, 2H), 3.36 (m, 2H), 2.85 (m, 1H), 2.66 (s, 3H), 1.78 (m, 2H), 1.61 (m, 2H), 1.44 (s, 9H).

Step 2. Synthesis of 22 from 21

A solution of 42.0 g (182 mmol) of 21 in 100 mL of methylene chloride was added dropwise to 180 mL of trifluoroacetic acid at 0° C. The resulting solution then was stirred at 25° C. for 2 h. The mixture was concentrated under vacuum, and the residue was dissolved in 10% aqueous sodium hydroxide solution. This aqueous solution was extracted repeatedly with methylene chloride. The combined extracts were dried over anhydrous sodium sulfate and then concentrated under vacuum to provide 21.00 g of 22 as a colorless oil. NMR (DMSO-d₆) δ 3.82 (m, 2H), 3.19 (m, 2H), 2.30 (s, 3H), 2.17 (m, 1H), 1.69 (m, 2H), 1.29 (m, 2H).

Step 3. Synthesis of 18 from 22

To a solution of 21.80 g (168 mmol) of 22 and 23.40 mL (168 mmol) of triethylamine in 500 mL of methylene chloride at 0° C. was added dropwise 21.00 mL (168 mmol) of phenyl chloroformate. The resulting mixture was stirred at 0° C. for 3 h, warmed slowly to 25° C., and then stirred at 25° C. for 16 h. The reaction mixture was washed with 0.1N hydrochloric acid, water, and brine, dried over anhydrous sodium sulfate, filtered, and concentrated under vacuum. The crude product was recyrstallized from 1-chlorobutane/hexane to furnish 29.00 g of 18 as a white solid. NMR (CDCl₃) δ 7.35 (t, 2H, J=9 Hz), 7.21 (t, 1H, J=9 Hz), 7.13 (d, 2H, J=9 Hz), 4.05 (m, 2H), 3.37 (m, 2H), 3.02 (m, 1H), 2.79 (s, 3H), 1.85 (m, 2H), 1.68 (m, 2H).

Example 14

Preparation of 3-(4-(4-methylpiperazino)phenyl)-5-((N-methyl-N-(4-tetrahydropyranyl)amino)carbamoylamino)-indeno [1,2-c]pyrazol-4-one

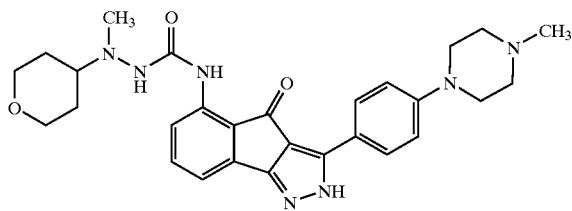

Prepared in a manner as described for example 2 employing example 13 as starting material. ESI-MS m/e calc'd for $C_{28}H_{34}N_7O_3$: 516.2723, found: 516.2744.

Example 15

Preparation of 3-(4-(4-ethylpiperazino)phenyl)-5-((N-methyl-N-(4-tetrahydropyranyl)amino)carbamoylamino)indeno [1,2-c]pyrazol-4-one

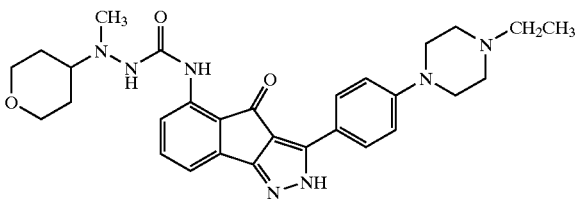

Prepared in a manner as described for example 2 employing example 13 and acetaldehyde as starting materials. ESI-MS m/e calc'd for $C_{29}H_{36}N_7O_3$: 530.2880, found: 530.2890.

Example 16

Preparation of 3-(4-(4-isopropylpiperazino)phenyl)-5-((N-methyl-N-(4-tetrahydropyranyl)amino)carbamoylamino)-indeno [1,2-c]pyrazol-4-one

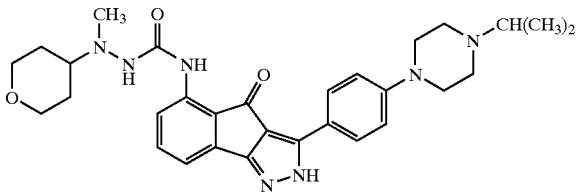

Prepared in a manner as described for example 2 employing example 13 and acetone as starting material. ESI-MS m/e calc'd for $C_{30}H_{38}N_7O_3$: 544.3036, found: 544.3055.

Example 17

Preparation of 3-(4-(4-piperazinophenyl)-5-((N-methyl-N-cyclohexylamino)carbamoylamino)-indeno [1,2-c]pyrazol-4-one

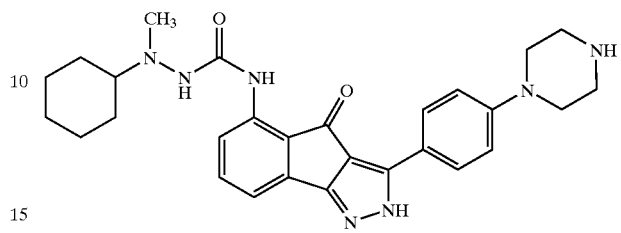

Prepared in a manner as described for example 13 employing 14 and the cyclohexyl analog of 18 [prepared as described for the synthesis of 18] as starting materials. ESI-MS m/e calc'd for $C_{28}H_{34}N_7O_2$: 500.2774, found: 500.2773.

Example 18

Preparation of 3-(4-(4-methylpiperazino)phenyl)-5-((N-methyl-N-cyclohexylamino)carbamoylamino)-indeno [1,2-c]pyrazol-4-one

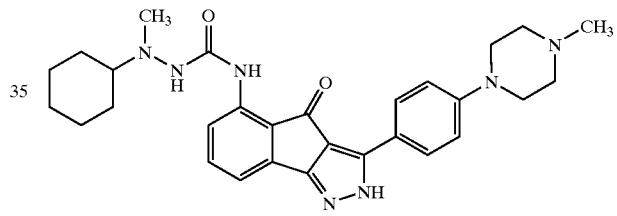

Prepared in a manner as described for example 2 employing example 17 as starting material. ESI-MS m/e calc'd for $C_{29}H_{36}N_7O_2$: 514.2931, found: 514.2937.

Example 19

Preparation of 3-(4-(4-ethylpiperazino)phenyl)-5-((N-methyl-N-cyclohexylamino)carbamoylamino)indeno [1,2-c]pyrazol-4-one

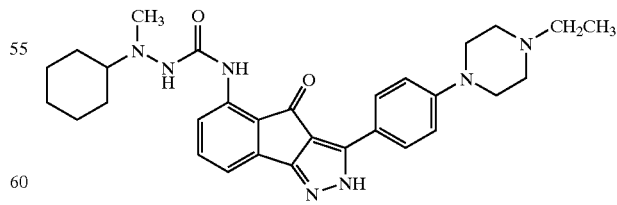

Prepared in a manner as described for example 2 employing example 17 and acetaldehyde as starting materials. ESI-MS m/e calc'd for $C_{30}H_{38}N_7O_2$: 528.3087, found: 528.3088.

Example 20

Preparation of 3-(4-(4-isopropylpiperazino)phenyl)-5-((N-methyl-N-cyclohexylamino)carbamoylamino)-indeno [1,2-c]pyrazol-4-one

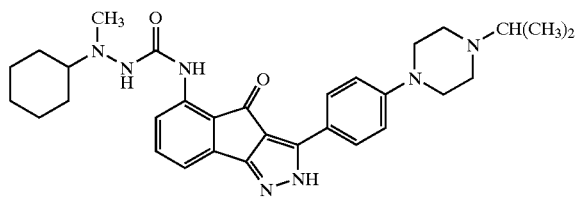

Prepared in a manner as described for example 2 employing example 17 and acetone as starting material. ESI-MS m/e calc'd for $C_{31}H_{40}N_7O_2$: 542.3243, found: 542.3242.

Example 21

Preparation of 3-(4-piperazinophenyl)-5-((N-methyl-N-(1-methylpiperidin-4-yl)amino)carbamoylamino)indeno [1,2-c]pyrazol-4-one

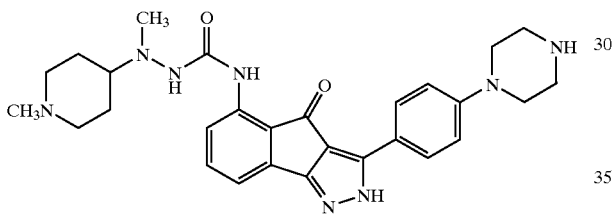

Prepared in a manner as described for example 13 employing 14 and the 1-methylpiperidin-4-yl analog of 18 [prepared as described for the synthesis of 18] as starting materials. ESI-MS m/e calc'd for $C_{28}H_{35}N_8O_2$: 515.2883, found: 515.2902.

Example 22

Preparation of 3-(4-homopiperazinophenyl)-5-((N-methyl-N-(4-tetrahydropyranyl)amino)carbamoylamino)indeno [1,2-c]pyrazol-4-one

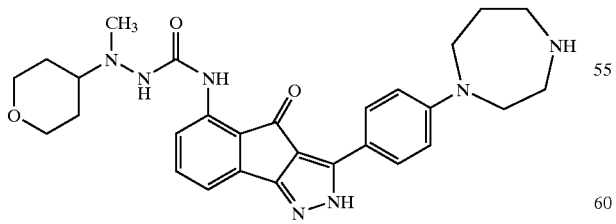

Prepared in a manner as described for examples 1 and 13 employing 4-(4-t-butoxycarbonyl-homopiperazino) acetophenone and 18 as starting materials. ESI-MS m/e calc'd for $C_{28}H_{34}N_7O_3$: 516.2723, found: 516.2741.

Example 23

Preparation of 3-(4-(4-methylhomopiperazino)phenyl)-5-((N-methyl-N-(4-tetrahydropyranyl)amino)carbamoylamino)-indeno [1,2-c]pyrazol-4-one

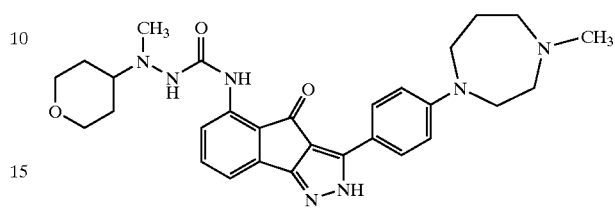

Prepared in a manner as described for example 2 employing example 22 as starting material. ESI-MS m/e calc'd for $C_{29}H_{36}N_7O_3$: 530.2880, found: 530.2892.

Example 24

Preparation of 3-(4-(4-ethylhomopiperazino)phenyl)-5-((N-methyl-N-(4-tetrahydropyranyl)amino)carbamoylamino)-indeno [1,2-c]pyrazol-4-one

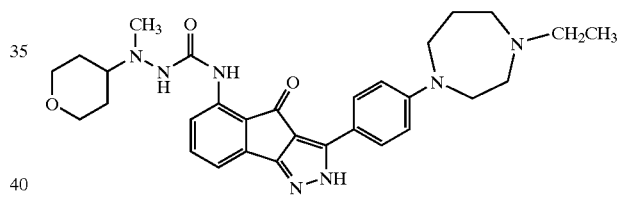

Prepared in a manner as described for example 2 employing example 22 and acetaldehyde as starting materials. ESI-MS m/e calc'd for $C_{30}H_{38}N_7O_3$: 544.3036, found: 544.3048.

Example 25

Preparation of 3-(4-(4-isopropylhomopiperazino)phenyl)-5-((N-methyl-N-(4-tetrahydropyranyl)amino)carbamoylamino)-indeno [1,2-c]pyrazol-4-one

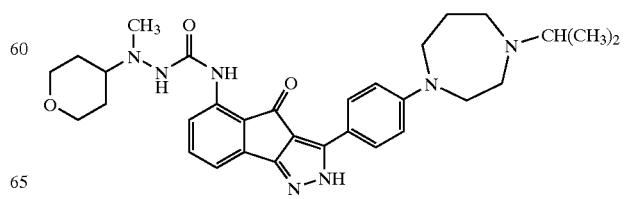

Prepared in a manner as described for example 2 employing example 22 and acetone as starting materials. ESI-MS m/e calc'd for $C_{31}H_{40}N_7O_3$: 558.3192, found: 558.3196.

Example 26

Preparation of 3-(4-(4-(N,N-dimethylamino)piperidino)phenyl)-5-((N-methyl-N-(4-tetrahydropyranyl)amino)carbamoylamino)-indeno[1,2-c]pyrazol-4-one

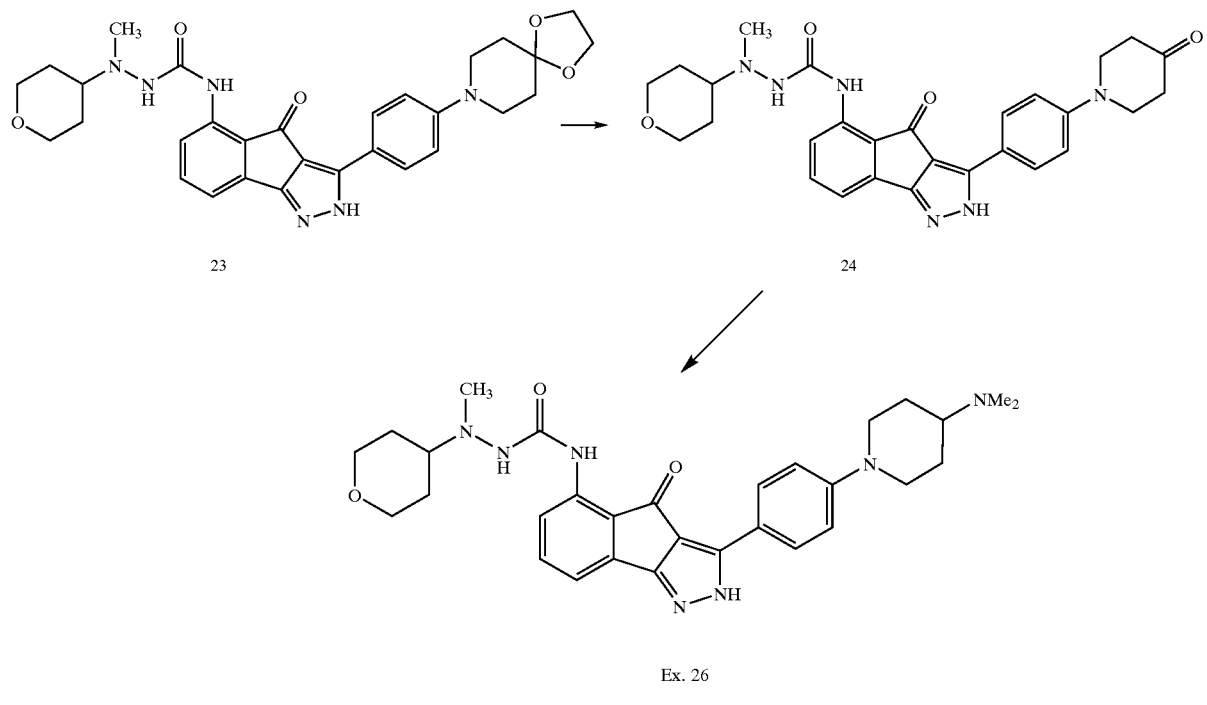

Ex. 26

Step 1. Synthesis of 23

Prepared in a similar fashion as described for examples 1 and 13 employing 4-(4,4-ethylenedioxypiperidino)-acetophenone and 18 as starting materials.

Step 2. Synthesis of 24 from 23

A mixture of 3.20 g (5.7 mmol) of 23, 300 mL of acetone, 75 mL of water, and 15 mL of trifluoroacetic acid was refluxed for 6 h. After cooling to room temperature the mixture was concentrated under vacuum. The residue was slurried in 95% aqueous ethanol, and the mixture was adjusted to pH 7 employing conc. aqueous ammonium hydroxide. The resulting mixture was filtered. The recovered solids were washed with ethanol and dried to afford 2.80 g of 24 as a yellow solid.

Step 3. Synthesis of Ex. 26 from 24

To a mixture of 2.57 g (5.0 mmol) of 24, 500 mL of 2M dimethylamine in methanol, 500 mL of acetonitrile, and 5 mL of acetic acid at 25° C. was added 6.28 g (100 mmol) of sodium cyanoborohydride, and the reaction mixture was stirred at 25° C. for 20 h. The mixture was diluted with 500 mL of water and then acidified (pH<2) employing conc. hydrochloric acid. After 30 min. gas evolution had ceased, and the solution was made strongly basic (pH>12) employing conc. aqueous sodium hydroxide solution. The solution was stirred for 20 min. and then was adjusted to pH 10 by the addition of 1N hydrochloric acid. The resulting precipitate was recovered by filtration, washed with water, and dried. These solids were dissolved in 20 mL of acetic acid, and the solution was diluted with 100 mL of anhydrous ethanol. A yellow precipitate form, was recovered by filtration, and was dried under vacuum to provide 1.68 g of the product as its acetate salt. ESI-MS m/e calc'd for $C_{30}H_{38}N_7O_3$: 544.3036, found: 544.3034.

Example 27

Preparation of 3-(4-(4-pyrrolidinopiperidino)phenyl)-5-((N-methyl-N-(4-tetrahydropyranyl)amino)carbamoylamino)-indeno[1,2-c]pyrazol-4-one

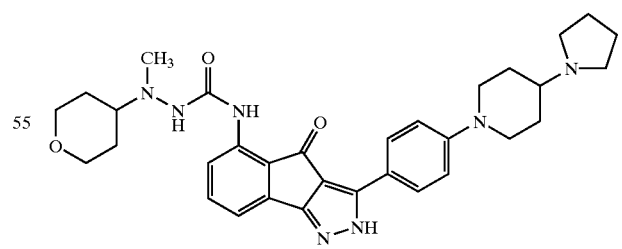

Prepared in a manner as described for example 26 employing 24 and pyrrolidine as starting materials. ESI-MS m/e calc'd for $C_{32}H_{40}N_7O_3$: 570.3193, found: 570.3192.

Example 28

Preparation of 3-(4-(4-piperidinopiperidino)phenyl)-5-((N-methyl-N-(4-tetrahydropyranyl) amino) carbamoylamino)-indeno [1,2-c]pyrazol-4-one

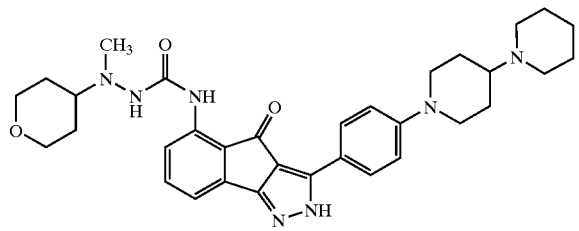

Prepared in a manner as described for example 26 employing 24 and pyrrolidine as starting materials. ESI-MS m/e calc'd for $C_{33}H_{42}N_7O_3$: 584.3349, found: 584.3349.

Example 29

Preparation of 3-(2,4-dimethylthiazol-5-yl)-5-((N-methyl-N-(4-tetrahydropyranyl)amino) carbamoylamino)indeno [1,2-c]pyrazol-4-one

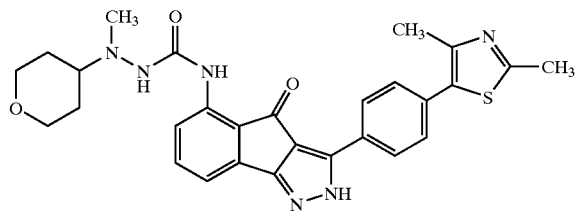

Prepared in a manner as described for examples 1 and 13 employing 5-acetyl-2,4-dimethylthiazole and 18 as starting materials. ESI-MS m/e calc'd for $C_{22}H_{25}N_6O_3S$: 453.1709, found: 453.1732.

The compounds useful according to the invention optionally are supplied as salts. Those salts which are pharmaceutically acceptable are of particular interest since they are useful in administering the foregoing compounds for medical purposes. Salts which are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Where the compound useful according to the invention contains a carboxy group, or a sufficiently acidic bioisostere, base addition salts may be formed and are simply a more convenient form for use; and in practice, use of the salt form inherently amounts to use of the free acid form.

Also, where the compound useful according to the invention contains a basic group, or a sufficiently basic bioisostere, acid addition salts may be formed and are simply a more convenient form for use; and in practice, use of the salt form inherently amounts to use of the free base form.

The foregoing compounds useful according to the invention may also be mixed another therapeutic compound to form pharmaceutical compositions (with or without diluent or carrier) which, when administered, provide simultaneous administration of a combination of active ingredients resulting in the combination therapy of the invention.

While it is possible for the compounds useful according to the invention to be administered alone it is preferably to present them as pharmaceutical compositions. The pharmaceutical compositions, both for veterinary and for human use, useful according to the present invention comprise at lease one compound of the invention, as above defined, together with one or more acceptable carriers therefor and optionally other therapeutic ingredients.

In certain preferred embodiments, active ingredients necessary in combination therapy may be combined in a single pharmaceutical composition for simultaneous administration.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The oily phase of the emulsions of this invention may be constituted from known ingredients in a known manner. While the oily phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the way together with the oil and fat make up the emulsifying ointment base which forms the oily dispersed phase of a cream formulation. Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

If desired, the aqueous phase of the cream base may include, for example, a least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogue.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used. Solid compositions of may also be employed as fillers in soft and hard-filled gelatin capsules using such excipients as lactose or milk sugar as well as high molecular weight polyethylene glycols, and the like.

The pharmaceutical compositions can be administered in a suitable formulation to humans and animals by topical or systemic administration, including oral, inhalational, rectal, nasal, buccal, sublingual, vaginal, parenteral (including subcutaneous, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein.

Solid compositions for rectal administration include suppositories formulated in accordance with known methods and containing at least one compound of the invention.

If desired, and for more effective distribution, the compounds can be microencapsulated in, or attached to, a slow release or targeted delivery systems such as a biocompatible, biodegradable polymer matrices (e.g. poly(d,l-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds useful according to this invention administered to a host in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The amount of each component administered is determined by the attending clinicians taking into consideration the etiology and severity of the disease, the patient's condition and age, the potency of each component and other factors.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Administration of a compound of the present invention in combination with additional therapeutic agents, may afford an efficacy advantage over the compounds and agents alone, and may do so while permitting the use of lower doses of each. A lower dosage minimizes the potential of side effects, thereby providing an increased margin of safety. The combination of a compound of the present invention with such additional therapeutic agents is preferably a synergistic combination. Synergy, as described for example by Chou and Talalay, Adv. Enzyme Regul. 22:27–55 (1984), occurs when the therapeutic effect of the compound and agent when administered in combination is greater than the additive effect of the either the compound or agent when administered alone. In general, a synergistic effect is most clearly demonstrated at levels that are (therapeutically) sub-optimal for either the compound of the present invention or a known anti-proliferative agent alone, but which are highly efficacious in combination. Synergy can be in terms of improved inhibitory response without substantial increases in toxicity over individual treatments alone, or some other beneficial effect of the combination compared with the individual components.

The compounds of the invention, their methods or preparation and their biological activity will appear more clearly from the examination of the following examples which are presented as an illustration only and are not to be considered as limiting the invention in its scope.

Procedures for evaluating the biological activity of compounds or compositions according to the invention are carried out as described herein or by the application or adaptation of known procedures, by which is meant procedures used heretofore or as described in the literature.

Utility

Inhibition of Kinase/Cyclin Complex Enzymatic Activity

Several of the compounds disclosed in this invention were assayed for their inhibitory activity against cdk4/D1 and cdk2/E kinase complexes. Briefly, the in vitro assays employ cell lysates from insect cells expressing either of the kinases and subsequently their corresponding regulatory units. The cdk2/cyclinE is purified from insect cells expressing His-tagged cdk2 and cyclin E. The cdk/cyclin lysate is combined in a microtiter-type plate along with a kinase compatible buffer, $^{32}$P-labeled ATP at a concentration of 50 mM, a GST-Rb fusion protein and the test compound at varying concentrations. The kinase reaction is allowed to proceeded with the radiolabed ATP, then effectively stopped by the addition of a large excess of EDTA and unlabeled ATP. The GST-Rb labeled protein is sequestered on a GSH-Sepharose bead suspension, washed, resuspended in scintillant, and the $^{32}$p activity detected in a scintillation counter. The compound concentration which inhibits 50% of the kinase activity was calculated for each compound. A compound was considered active if its IC$_{50}$ was found to be less than 1 μM.

Inhibition of HCT 116 Cancer Cell Proliferation

To test the cellular activity of several compounds disclosed in this invention, we examined the effect of these compounds on cultured HCT116 cells and determined their effect on cell-cycle progression by the calorimetric cytotoxcity test using sulforhodamine B (Skehan et al. *J. Natl. Cancer Inst.* 82:1107–12, 1990). Briefly, HCT116 cells are cultured in the presence of test compounds at increasing concentrations. At selected time points, groups of cells are fixed with trichloroacetic acid and stained with sulforhodamine B (SRB). Unbound dye was removed by washing and protein-bound dye was extracted for determination of optical density. A compound was considered active if its IC$_{50}$ was found to be less than 10 μM.

What is claimed is:

1. A compound according to formula (I):

X is selected from O or S;

R$^1$ is selected from the groups: C3–C10 membered carbocycle substituted with 0–5 R$^4$, and 3–10 membered heterocycle substituted with 0–5 R$^5$, provided that if R$^1$ is phenyl then R$^1$ is substituted with 1–5 R$^4$;

R$^2$ is selected from the groups: H, C$_{1-10}$ alkyl substituted with 0–3 R$^6$, C$_{2-10}$ alkenyl substituted with 0–3 R$^6$, C$_{2-10}$ alkynyl substituted with 0–3 R$^6$, —(CF$_2$)$_m$CF$_3$, C$_{3-10}$ membered carbocycle substituted with 0–5 R$^4$, and 3–10 membered heterocycle containing from 1–4 heteroatoms selected from O, N, and S and substituted with 0–5 R$^5$;

R$^3$ is selected from the groups: H, C$_{1-4}$ alkyl, C$_{3-6}$ cycloalkyl, or C$_{4-10}$ cycloalkylalkyl;

R$^4$ independently selected from the groups: halo, —CN, NO$_2$, C$_{1-4}$ alkyl, C$_{1-4}$ haloalkyl, NR$^7$R$^{7a}$, =O, OR$^7$, COR$^7$, CO$_2$R$^7$, CONR$^7$R$^{7a}$, NHC(O)NR$^7$R$^{7a}$, NHC(S)NR$^7$R$^{7a}$, NR$^7$C(O)OR$^{7b}$, NR$^7$C(O)R$^{7b}$SO$_2$NR$^7$R$^{7a}$, SO$_2$R$^{7b}$, and 5–10 membered heterocycle containing from 1–4 heteroatoms selected from O, N, and S;

alternatively, when two R$^4$'s are present on adjacent carbon atoms they combine to form —OCH$_2$O— or —OCH$_2$CH$_2$O—;

R$^5$ is independently selected from the groups: halo, —CN, NO$_2$, C$_{1-4}$ alkyl, C$_{1-4}$ haloalkyl, NR$^7$R$^{7a}$, NR$^7$C(O) OR$^{7b}$, NR$^7$C(O)R$^{7b}$, OR$^7$, COR$^7$, CO$_2$R$^7$, CONR$^7$R$^{7a}$, CON(R$^9$)[(CH$_2$)$_m$R$^{10}$], CO(CH$_2$)$_m$R$^{10}$, NHC(O) NR$^7$R$^{7a}$, NHC(S)NR$^7$R$^{7a}$, SO$_2$NR$^7$R$^{7a}$, and SO$_2$R$^{7b}$;

R$^6$ is independently selected from the groups: halo, —CN, NO$_2$, C$_{1-4}$ alkyl, C$_{1-4}$ haloalkyl, NR$^7$R$^{7a}$, NR$^8$NR$^8$R$^{8a}$, NR$^7$C(O)OR$^7$, NR$^7$C(O)R$^{7b}$, =O, OR$^7$, COR$^7$, CO$_2$R$^7$, CONR$^7$R$^{7a}$, NHC(O)NR$^7$R$^{7a}$, NHC(S) NR$^7$R$^{7a}$, SO$_2$N$^7$R$^{7a}$, SO$_2$R$^{7b}$, C$_{3-10}$ membered carbocycle substituted with 0–5 R$^4$, and 5–10 membered heterocycle containing from 1–4 heteroatoms selected from O, N, and S, substituted with 0–3 R$^7$;

R$^7$ is independently selected from the groups: H, halo, —CN, NO$_2$, C$_{1-4}$ haloalkyl, R$^8$R$^{8a}$N(CR$^9$R$^{9a}$)$_m$, NR$^8$NR$^8$R$^{8a}$, NR$^8$C(O)OR$^8$, NR$^8$C(O)R$^8$, =O, R$^8$O (CR$^9$R$^{9a}$)$_m$, COR$^8$, CO$_2$R$^8$, CONR$^8$R$^{8a}$, NHC(O) NR$^8$R$^{8a}$, NHC(S)NR$^8$R$^{8a}$, SO$_2$NR$^8$R$^{8a}$, SO$_2$R$^{8b}$, C$_{1-4}$alkyl, C$_{3-6}$cycloalkyl, C$_{4-10}$cycloalkylalkyl, phenyl, and benzyl;

R$^{7a}$ is independently selected from the groups: H, C$_{1-4}$ alkyl, C$_{3-6}$ cycloalkyl, C$_{4-10}$ cycloalkylalkyl, phenyl, and benzyl;

alternatively, R$^7$ and R$^{7a}$, together with the atoms to which they are attached, form a heterocycle having 4–8 atoms in the ring and containing an additional 0–1 N, S, or O atom and substituted with 0–3 R$^{7c}$;

R$^{7b}$ is independently selected from the groups: H, C$_{1-4}$ alkyl, C$_{3-6}$ cycloalkyl, C$_{4-10}$ cycloalkylalkyl, phenyl, and benzyl;

R$^{7c}$ is independently selected from the groups: halo, —CN, N$_3$, NO$_2$, C$_{1-4}$ alkyl, C$_{3-6}$ cycloalkyl, C$_{4-10}$ cycloalkylalkyl, C$_{1-4}$ haloalkyl, NR$^7$R$^{7b}$, R$^8$R$^{8a}$N (CR$^9$R$^{9a}$)$_m$, =O, OR$^7$, R$^8$O(CR$^9$R$^{9a}$)$_m$, COR$^7$, C$_2$R$^7$, CONR$^7$R$^{7b}$, NHC(O)NR$^7$R$^{7b}$, NHC(S)NR$^7$R$^{7b}$, NR$^7$C (O)OR$^{7b}$, NR$^7$C(O)R$^{7b}$, C(=NR$^8$)R$^{8a}$, C(=NR$^8$) NR$^{8a}$R$^{8b}$, SO$_2$NR$^7$R$^{7b}$, SO$_2$R$^{7b}$, and 5–10 membered heterocycle containing from 1–4 heteroatoms selected from O, N, and S;

R$^8$ is independently selected from the groups: H, C$_{1-4}$ alkyl, C$_{3-6}$ cycloalkyl, C$_{4-10}$ cycloalkylalkyl, phenyl and benzyl;

R$^{8a}$ is independently selected from the groups: H, C$_{1-4}$ alkyl, C$_{3-6}$ cycloalkyl, C$_{4-10}$ cycloalkylalkyl, phenyl and benzyl;

alternatively, R$^8$ and R$^{8a}$, together with the atoms to which they are attached, form a heterocycle having 4–8 atoms in the ring and containing an additional 0–1 N, S, or O atom;

R$^{8b}$ is independently selected from the groups: H, C$_{1-4}$ alkyl, C$_{3-6}$ cycloalkyl, C$_{4-10}$ cycloalkylalkyl, phenyl and benzyl;

R$^9$ is independently selected from the groups: H, C$_{1-4}$ alkyl;

R$^{9a}$ is independently selected from the groups: H, C$_{1-4}$ alkyl;

R$^{10}$ is independently selected from the groups: NR$^7$R$^{7a}$, C$_{3-10}$ membered carbocycle substituted with 0–3 R$^7$, and 5–10 membered heterocycle containing from 1–4 heteroatoms selected from O, N, and S, substituted with 0–3 R$^7$; and m is independently selected from 0,1,2,3, and 4;

or a pharmaceutically acceptable salt thereof, an N-oxide form thereof, or a stereoisomer thereof.

2. A compound according to claim 1, wherein:

X is O;

R$^1$ is selected from the groups: C$_5$–C$_6$ membered carbocycle substituted with 0–5 R$^4$, and 5–6 membered heterocycle substituted with 0–5 R$^5$.

3. A compound according to claim 1, wherein:
X is O;
$R^1$ is a $C_5$–$C_6$ membered carbocycle substituted with 0–5 $R^4$, wherein the carbocycle is an aryl, cycloalkyl, or cycloalkenyl group.

4. A compound according to claim 1, wherein:
X is O;
$R^1$ is phenyl substituted with 0–5 $R^4$.

5. A compound according to claim 1, wherein:
X is O;
$R^1$ is a $C_5$–$C_6$ membered cycloalkyl group substituted with 0–5 $R^4$, wherein the cycloalkyl is cyclohexyl, cyclopentyl.

6. A compound according to claim 1, wherein:
X is O;
$R^1$ is a $C_5$–$C_6$ membered cycloalkenyl group substituted with 0–5 $R^4$, wherein the cycloalkenyl group is cyclohexenyl, cyclopentenyl.

7. A compound according to claim 1, wherein:
X is O;
$R^1$ is a $C_5$–$C_7$ membered heterocycle substituted with 0–5 $R^5$, wherein the heterocycle is a heteroaryl, heterocyclenyl, or heterocyclyl group.

8. A compound according to claim 1, wherein:
X is O;
$R^1$ is a $C_5$–$C_6$ membered heteroaryl substituted with 0–5 $R^5$, wherein the heteroaryl is pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl or triazolyl.

9. A compound according to claim 1, wherein:
X is O;
$R^1$ is a $C_5$–$C_6$ membered heteroaryl substituted with 0–5 $R^5$, wherein the heteroaryl is pyrazinyl, pyridazinyl, pyridyl, pyrimidinyl, thiazolyl or thienyl.

10. A compound according to claim 1, wherein:
X is O;
$R^1$ is a $C_5$–$C_6$ membered heterocyclyl substituted with 0–5 $R^5$, wherein the heterocyclyl is tetrahydropyranyl, pyrrolidinyl, imidazolidinyl, pyrazolidinyl, piperidinyl, morpholinyl, thiomorpholinyl, or piperazinyl.

11. A compound according to claim 1, wherein:
X is O;
$R^1$ is a $C_5$–$C_6$ membered heterocyclyl substituted with 0–5 $R^5$, wherein the heterocyclyl is tetrahydropyranyl or morpholinyl.

12. A compound according to claim 1, wherein:
X is O;
$R^1$ is a $C_5$–$C_6$ membered heterocyclenyl group substituted with 0–5 $R^5$, wherein the heterocyclenyl group is 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, 3,4-dihydro-2H-pyran, or dihydrofuranyl.

13. A compound according to claim 1, wherein:
X is O;
$R^3$ is selected from the groups: H, $C_{1-4}$ alkyl.

14. A compound according to claim 1, wherein:
X is O;
$R^3$ is methyl.

15. A compound according to claim 1, wherein:
X is O;
$R^2$ is a $C_3$–$C_{10}$ membered carbocycle substituted with 0–5 $R^4$, or a 3–10 membered heterocycle containing from 1–4 heteroatoms selected from O, N, and S and substituted with 0–5 $R^5$.

16. A compound according to claim 1, wherein:
X is O;
$R^2$ is $C_5$–$C_6$ membered carbocycle substituted with 0–5 $R^4$, wherein the carbocycle is an aryl, cycloalkyl, or cycloalkenyl group.

17. A compound according to claim 1, wherein:
X is O;
$R^2$ is phenyl substituted with 0–5 $R^4$.

18. A compound according to claim 1, wherein:
X is O;
$R^2$ is cycloalkyl substituted with 0–5 $R^4$, a $C_5$–$C_6$ membered cycloalkyl group substituted with 0–5 $R^4$, wherein the cycloalkyl is cyclohexyl, cyclopentyl.

19. A compound according to claim 1, wherein:
X is O;
$R^2$ is a $C_5$–$C_6$ membered cycloalkenyl group substituted with 0–5 $R^4$, wherein the cycloalkenyl group is cyclohexenyl, cyclopentenyl.

20. A compound according to claim 1, wherein:
X is O;
$R^2$ is a $C_5$–$C_7$ membered heterocycle substituted with 0–5 $R^5$, wherein the heterocycle is a heteroaryl, heterocyclenyl, or heterocyclyl group.

21. A compound according to claim 1, wherein:
X is O;
$R^2$ is a $C_5$–$C_6$ membered heteroaryl substituted with 0–5 $R^5$, wherein the heteroaryl is pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl or triazolyi.

22. A compound according to claim 1, wherein:
X is O;
$R^2$ is a $C_5$–$C_6$ membered heteroaryl substituted with 0–5 $R^5$, wherein the heteroaryl is pyrazinyl, pyridazinyl, pyridyl, pyrimidinyl, thiazolyl or thienyl.

23. A compound according to claim 1, wherein:
X is O;
$R^2$ is a $C_5$–$C_6$ membered heterocyclyl substituted with 0–5 $R^5$, wherein the heterocyclyl is tetrahydropyranyl, pyrrolidinyl, imidazolidinyl, pyrazolidinyl, piperidinyl, morpholinyl, thiomorpholinyl, or piperazinyl.

24. A compound according to claim 1, wherein:

X is O;

$R^2$ is a $C_5$–$C_6$ membered heterocyclenyl group substituted with 0–5 $R^5$, wherein the heterocyclenyl group is 1,2,3,4-tetrahydrohydropyridine, 1,2-dihydropyridyl, 1,4-dihydropyridyl, 1,2,3,6-tetrahydropyridine, 1,4,5,6-tetrahydropynmidine, 2-pyrrolinyl, 3-pyrrolinyl, 2-imidazolinyl, 2-pyrazolinyl, 3,4-dihydro-2H-pyran, or dihydrofuranyl.

25. A compound according to claim 1, wherein:

X is O;

$R^2$ is phenyl substituted with 1–5 $R^4$.

26. A compound according to claim 1, wherein:

X is O;

$R^2$ is phenyl substituted with 1–4 $R^4$.

27. A compound according to claim 1, wherein:

X is O;

$R^2$ is phenyl substituted with 1–3 $R^4$.

28. A compound according to claim 1, wherein:

X is O;

$R^2$ is phenyl substituted with 1–2 $R^4$.

29. A compound according to claim 1, wherein:

X is O;

$R^2$ is phenyl substituted with $R^4$;

$R^4$ is a 5–10 membered heterocycle containing from 1–4 heteroatoms selected from O, N, and S, wherein the heterocycle is a heteroaryl, heterocyclenyl, or heterocyclyl group.

30. A compound according to claim 1, wherein:

X is O;

$R^2$ is phenyl substituted with $R^4$;

$R^4$ is a 5–6 membered heteroaryl containing from 1–4 heteroatoms selected from O, N, and S, which is substituted with 0–5 $R^5$.

31. A compound according to claim 1, wherein:

X is O;

$R^2$ is phenyl substituted with $R^4$;

$R^4$ is $NR^7R^{7a}$.

32. A compound according to claim 1, wherein:

X is O;

$R^2$ is phenyl substituted with $R^4$;

$R^4$ is $NR^7R^{7a}$;

$R^7$ and $R^{7a}$, together with the atoms to which they are attached, form a heterocycle having 4–8 atoms in the ring and containing an additional 0–1 N, S, or O atom and substituted with 0–3 $R^{7c}$; and $R^{7c}$ is independently selected from the groups: halo, —CN, $N_3$, $NO_2$, $C_{1-4}$ alkyl, $C_{3-6}$ cycloalkyl, $C_{4-10}$ cycloalkylalkyl, $C_{1-4}$ haloalkyl, $NR^7R^{7b}$, $R^8R^{8a}N(CR^9R^{9a})_m$, =O, $OR^7$, $R^8O(CR^9R^{9a})_m$, $COR^7$, $CO_2R^7$, $CONR^7R^{7b}$, $NHC(O)NR^7R^{7b}$, $NHC(S)NR^7R^{7b}$, $NR^7C(O)OR^{7b}$, $NR^7C(O)R^{7b}$, $C(=NR^8)R^{8a}$, $C(=NR^8)NR^{8a}R^{8b}$, $SO_2NR^7R^{7b}$, $SO_2R^{7b}$, and 5–10 membered heterocycle containing from 1–4 heteroatoms selected from O, N, and S.

33. A compound according to claim 1, wherein:

X is O;

$R^2$ is phenyl substituted with $R^4$;

$R^4$ is $NR^7R^{7a}$;

$R^7$ and $R^{7a}$, together with the atoms to which they are attached, form a heterocycle having 6–7 atoms in the ring and containing an additional 0–1 N atoms and substituted with 0–3 $R^{7c}$; and $R^{7c}$ is independently selected from the groups: halo, —CN, $N_3$, $NO_2$, $C_{1-4}$ alkyl, $C_{3-6}$ cycloalkyl, $C_{4-10}$ cycloalkylalkyl, $C_{1-4}$ haloalkyl, $NR^7R^{7b}$, $R^8R^{8a}N(CR^9R^{9a})_m$, =O, $OR^7$, $R^8O(CR^9R^{9a})_m$, $COR^7$, $CO_2R^7$, $CONR^7R^{7b}$, $NHC(O)NR^7R^{7b}$, $NHC(S)NR^7R^{7b}$, $NR^7C(O)OR^{7b}$, $NR^7C(O)R^{7b}$, $C(=NR^8)R^{8a}$, $C(=NR^8)NR^{8a}R^{8b}$, $SO_2NR^7R^{7b}$, $SO_2R^{7b}$, and 5–10 membered heterocycle containing from 1–4 heteroatoms selected from O, N, and S.

34. A compound according to claim 1, wherein:

X is O;

$R^2$ is phenyl substituted with $R^4$;

$R^4$ is $NR^7R^{7a}$;

$R^7$ and $R^{7a}$, together with the atoms to which they are attached, form a 6–7 membered heterocyclyl group or a 6–7 membered heterocyclenyl group, substituted with 0–3 $R^{7c}$; and $R^{7c}$ is independently selected from the groups: halo, —CN, $N_3$, $NO_2$, $C_{1-4}$ alkyl, $C_{3-6}$ cycloalkyl, $C_{4-10}$ cycloalkylalkyl, $C_{1-4}$ haloalkyl, $NR^7R^{7b}$, $R^8R^{8a}N(CR^9R^{9a})_m$, =O, $OR^7$, $R^8O(CR^9R^{9a})_m$, $COR^7$, $CO_2R^7$, $CONR^7R^{7b}$, $NHC(O)NR^7R^{7b}$, $NHC(S)NR^7R^{7b}$, $NR^7C(O)OR^{7b}$, $NR^7C(O)R^{7b}$, $C(=NR^8)R^{8a}$, $C(=NR^8)NR^{8a}R^{8b}$, $SO_2NR^7R^{7b}$, $SO_2R^{7b}$, and 5–10 membered heterocycle containing from 1–4 heteroatoms selected from O, N, and S.

35. A compound according to claim 1, wherein:

X is O;

$R^2$ is phenyl substituted with $R^4$;

$R^4$ is $NR^7R^{7a}$;

$R^7$ and $R^{7a}$, together with the atoms to which they are attached, form a 6–7 membered heterocyclyl group substituted with 0–3 $R^{7c}$, wherein the heterocyclyl group is piperazinyl, or homopiperazinyl, and $R^{7c}$ is independently selected from the groups: halo, —CN, $N_3$, $NO_2$, $C_{1-4}$ alkyl, $C_{3-6}$ cycloalkyl, $C_{4-10}$ cycloalkylalkyl, $C_{1-4}$ haloalkyl, $NR^7R^{7b}$, $R^8R^{8a}N(CR^9R^{9a})_m$, =O, $OR^7$, $R^8O(CR^9R^{9a})_m$, $COR^7$, $CO_2R^7$, $CONR^7R^{7b}$, $NHC(O)NR^7R^{7b}$, $NHC(S)NR^7R^{7b}$, $NR^7C(O)OR^{7b}$, $NR^7C(O)R^{7b}$, $C(=NR^8)R^{8a}$, $C(=NR^8)NR^{8a}R^{8b}$, $SO_2NR^7R^{7b}$, $SO_2R^{7b}$, and 5–10 membered heterocycle containing from 1–4 heteroatoms selected from O, N, and S.

36. A compound according to claim 1, wherein:

X is O;

$R^2$ is phenyl substituted with $R^4$;

$R^4$ is $NR^7R^{7a}$;

$R^7$ and $R^{7a}$, together with the atoms to which they are attached, form a 6–7 membered heterocyclenyl group substituted with 0–3 $R^{7c}$, wherein the heterocyclenyl group is, 2,3,4-tetrahydrohydropyridine, 1,2-dihydropyridyl, 1,4-dihydropyridyl, 1,2,3,6-tetrahydropyridine, or 1,4,5,6-tetrahydropyrimidine; and $R^{7c}$ is independently selected from the groups: halo, —CN, $N_3$, $NO_2$, $C_{1-4}$ alkyl, $C_{3-6}$ cycloalkyl, $C_{4-10}$ cycloalkylalkyl, $C_{1-4}$ haloalkyl, $NR^7R^{7b}$, $R^8R^{8a}N(CR^9R^{9a})_m$, =O, $OR^7$, $R^8O(CR^9R^{9a})_m$, $COR^7$, $CO_2R^7$, $CONR^7R^{7b}$, $NHC(O)NR^7R^{7b}$, $NHC(S)NR^7R^{7b}$, $NR^7C(O)OR^{7b}$, $NR^7C(O)R^{7b}$, $C(=NR^8)R^{8a}$, $C(=NR^8)NR^{8a}R^{8b}$, $SO_2NR^7R^{7b}$, $SO_2R^{7b}$, and 5–10 membered heterocycle containing from 1–4 heteroatoms selected from O, N, and S.

37. A compound according to claim 1, wherein:
$R^{7c}$ is independently selected from the groups: $C_{1-4}$ alkyl, $C_{3-6}$ cycloalkyl, $C_{4-10}$ cycloalkylalkyl, $NR^7R^{7b}$, and 5–10 membered heterocycle containing from 1–4 heteroatoms selected from O, N, and S.

38. A compound according to claim 1, wherein the compound is selected from:

3-(4-piperazinophenyl)-5-((N-methyl-N-(2-pyridinyl)amino)carbamoylammo)indeno[1,2-c]pyrazol-4-one;

3-(4-(4-methylpiperazino)phenyl)-5-((N-methyl-N-(2-pyridinyl)amino)carbamoylamino)indeno[1,2-c]pyrazol-4-one;

3-(4-homopiperazinophenyl)-5-((N-methyl-N-(2-pyridinyl)amino)carbamoylamino)indeno[1,2-c]pyrazol-4-one;

3-(4-(4-methylhomopiperazino)phenyl)-5-((N-methyl-N-(2-pyridinyl)amino)carbamoylamino)indeno[1,2-c]pyrazol-4-one;

3-(4-piperazinophenyl)-5-((N-methyl-N-(4-pyridinyl)amino)carbamoylamino)indeno[1,2-c]pyrazol-4-one;

3-(4-piperazinophenyl)-5-((N-methyl-N-(2-pyrazinyl)amino)carbamoylamino)indeno[1,2-c]pyrazol-4-one;

3-(4-piperazinophenyl)-5-((N-methyl-N-(2-pyrimidinyl)amino)carbamoylamino)indeno[1,2-c]pyrazol-4-one;

3-(4-piperazinophenyl)-5-((N-methyl-N-(2-thiazolyl)amino)carbaxnoylamino)indeno[1,2-c]pyrazol-4-one;

3-(4-piperazinophenyl)-5-((N-methyl-N-(3-pyridinyl)amino)carbamaylamino)indeno[1,2-c]pyrazol-4-one;

3-(4-(4-methylpiperazino)phenyl)-5-((N-methyl-N-(2-pyrazinyl)amino)carbamoylamino)indeno[1,2-c]pyrazol-4-one;

3-(4-(4-methylpiperazino)phenyl)-5-((N-methyl-N-(2-thiazolyl)axnino)carbamoylamino)indeno[1,2-c]pyrazol-4-one;

3-(4-(4-methylpiperazino)phenyl)-5-((N-methyl-N-(3-pyridinyl)amino)carbamoylamino)indeno[1,2-c]pyrazol-4-one;

3-(4-piperazinophenyl)-5-((N-methyl-N-(4-tetrahydropyranyl)amino)carbamoylamino)indeno[1,2-c]pyrazol-4-one;

3-(4-(4-methylpiperazino)phenyl)-5-((N-methyl-N-(4-tetrahydropyranyl)amino)carbamoylamino)-indeno[1,2-c]pyrazol-4-one;

3-(4-(4-ethylpiperazino)phenyl)-5-((N-methyl-N-(4-tetrahydropyranyl)amino)carbanioylamino)indeno[1,2-c]pyrazol-4-one;

3-(4-(4-isopropylpiperazino)phenyl)-5-((N-methyl-N-(4-tetrahydropyranyl)ainino)carbamoylamino)-indeno[1,2-c]pyrazol-4-one;

3-(4-(4-piperazinophenyl)-5-((N-methyl-N-cyclohexylamino)carbamoylamino)-indeno[1,2-c]pyrazol-4-one;

3-(4-(4-methylpiperazino)phenyl)-5-(( N-methyl-N-cyclohexylamino)carbamoylamino)-indeno[1,2-c]pyrazol-4-one;

3-(4-(4-ethylpiperazino)phenyl)-5-(( N-methyl-N-cyclohexylamino)carbamoylamino)indeno[1,2-c]pyrazol-4-one;

3-(4-(4-isopropylpiperazino)phenyl)-5-(( N-methyl-N-cyclohexylamino)carbamoylamino)-indeno[1,2-c]pyrazol-4-one;

3-(4-piperazinophenyl)-5-((N-methyl-N-(1-methylpiperidin-4-yl)amino)carbamoylamino)indeno[1,2-c]pyrazol-4-one;

3-(4-homopiperazinophenyl)-5-((N-methyl-N-(4-tetrahydropyranyl)amino)carbamoylamino)indeno[1,2-c]pyrazol-4-one;

3-(4-(4-methylhomopiperazino)phenyl)-5-((N-methyl-N-(4-tetrahydropyranyl)amino)carbamoylarnino)-indeno[1,2-c]pyrazol-4-one;

3-(4-(4-ethylhomopiperazino)phenyl)-5-((N-methyl-N-(4-tetrahydropyranyl)amino)carbamoylamino)-indeno[1,2-c]pyrazol-4-one;

3-(4-(4-isopropylhomopiperazino)pheflyl)-5-((N-methyl-N-(4-tetrahydropyranyl)amino)carbamoylamino)-indeno[1,2-c]pyrazol-4-one;

3-(4-(4-(N,N-dimethylamino)piperidino)phenyl)-5-((N-methyl-N-(4-tetrahydropyranyl)amino)carbamoylamino)-indeno[1,2-c]pyrazol-4-one;

3-(4-(4-pyrrolidinopiperidino)phenyl)-5-((N-methyl-N-(4-tetrahydropyranyl)amino)carbanioylamino)-indeno[1,2-c]pyrazol-4-one;

3-(4-(4-piperidinopiperidino)phenyl)-5-((N-methyl-N-(4-tetrahydropyranyl)amino)carbamoylamino)-indeno[1,2-c]pyrazol-4-one;

3-(2,4-dimethylthiazol-5-yl)-5-((N-methyl-N-(4-tetrahydropyranyl)amino)carbamoylamino)indeno[1,2-c]pyrazol-4-one; or pharmaceutically acceptable salt form thereof.

* * * * *